(12) United States Patent
Gibbons et al.

(10) Patent No.: US 10,908,093 B2
(45) Date of Patent: Feb. 2, 2021

(54) CALIBRATION OF FLUIDIC DEVICES

(71) Applicant: Labrador Diagnostics LLC, Wilmington, DE (US)

(72) Inventors: Ian Gibbons, Newark, CA (US); Chengwang Wang, Palo Alto, CA (US); Shaunak Roy, Palo Alto, CA (US); Elizabeth A. Holmes, Palo Alto, CA (US)

(73) Assignee: Labrador Diagnostics, LLC, Wilmington, DE (US)

( * ) Notice: Subject to any disclaimer, the term of this patent is extended or adjusted under 35 U.S.C. 154(b) by 0 days.

(21) Appl. No.: 14/867,271

(22) Filed: Sep. 28, 2015

(65) Prior Publication Data

US 2016/0116417 A1    Apr. 28, 2016

Related U.S. Application Data

(63) Continuation of application No. 12/986,954, filed on Jan. 7, 2011, now Pat. No. 9,182,388, which is a (Continued)

(51) Int. Cl.
*G01N 21/76* (2006.01)
*G01N 33/53* (2006.01)
(Continued)

(52) U.S. Cl.
CPC .......... *G01N 21/76* (2013.01); *A61B 5/1411* (2013.01); *A61B 5/1427* (2013.01); *A61B 5/14532* (2013.01); *A61B 5/157* (2013.01); *A61B 5/15142* (2013.01); *A61B 5/412* (2013.01); *A61B 5/417* (2013.01); (Continued)

(58) Field of Classification Search
CPC .......................... G01N 21/76; G01N 33/5302
See application file for complete search history.

(56) References Cited

U.S. PATENT DOCUMENTS

| | | | |
|---|---|---|---|
| 4,003,379 A | 1/1977 | Ellinwood, Jr. | |
| 4,146,029 A | 3/1979 | Ellinwood, Jr. | |

(Continued)

FOREIGN PATENT DOCUMENTS

| | | |
|---|---|---|
| CN | 1146017 A | 3/1997 |
| CN | 1173776 A | 2/1998 |

(Continued)

OTHER PUBLICATIONS

Office Action dated May 29, 2012 for U.S. Appl. No. 12/986,954.
(Continued)

*Primary Examiner* — Brian R Gordon
*Assistant Examiner* — Dwan A Gerido
(74) *Attorney, Agent, or Firm* — Sterne, Kessler, Goldstein & Fox P.L.L.C.

(57) ABSTRACT

The present invention provides methods of calibrating a fluidic device useful for detecting an analyte of interest in a bodily fluid. The invention also provides methods for assessing the reliability of an assay for an analyte in a bodily fluid with the use of a fluidic device. Another aspect of the invention is a method for performing a trend analysis on the concentration of an analyte in a subject using a fluidic device.

9 Claims, 23 Drawing Sheets

Related U.S. Application Data continuation of application No. 11/388,824, filed on Mar. 24, 2006, now Pat. No. 7,888,125.

(60) Provisional application No. 60/678,801, filed on May 9, 2005, provisional application No. 60/705,489, filed on Aug. 5, 2005, provisional application No. 60/717,192, filed on Sep. 16, 2005, provisional application No. 60/721,097, filed on Sep. 28, 2005.

(51) Int. Cl.
| | |
|---|---|
| B01L 3/00 | (2006.01) |
| A61B 5/151 | (2006.01) |
| A61B 5/157 | (2006.01) |
| A61B 5/145 | (2006.01) |
| A61B 5/00 | (2006.01) |
| G16H 40/63 | (2018.01) |
| A61B 5/15 | (2006.01) |
| G01N 33/50 | (2006.01) |
| A61B 5/155 | (2006.01) |
| G01N 33/543 | (2006.01) |
| A61B 5/1495 | (2006.01) |

(52) U.S. Cl.
CPC .......... *B01L 3/50273* (2013.01); *G01N 33/50* (2013.01); *G01N 33/53* (2013.01); *G01N 33/5302* (2013.01); *G01N 33/54386* (2013.01); *G16H 40/63* (2018.01); *A61B 5/1495* (2013.01); *A61B 5/14546* (2013.01); *A61B 5/150022* (2013.01); *A61B 5/150099* (2013.01); *A61B 5/150251* (2013.01); *A61B 5/150763* (2013.01); *A61B 5/150854* (2013.01); *B01L 2300/021* (2013.01); *B01L 2300/023* (2013.01); *B01L 2300/044* (2013.01); *B01L 2300/0636* (2013.01); *B01L 2300/087* (2013.01); *B01L 2300/0816* (2013.01); *B01L 2300/0867* (2013.01); *B01L 2300/0877* (2013.01); *B01L 2300/0883* (2013.01); *B01L 2300/0887* (2013.01); *G01N 2500/00* (2013.01); *Y02A 90/10* (2018.01); *Y10T 436/10* (2015.01); *Y10T 436/11* (2015.01); *Y10T 436/115831* (2015.01); *Y10T 436/12* (2015.01); *Y10T 436/143333* (2015.01)

(56) References Cited

U.S. PATENT DOCUMENTS

| | | |
|---|---|---|
| 4,347,176 A | 8/1982 | Mehta |
| 4,731,726 A | 3/1988 | Allen |
| 4,793,825 A | 12/1988 | Benjamin et al. |
| 4,910,131 A | 3/1990 | Mellman et al. |
| 4,920,213 A | 4/1990 | Dale et al. |
| 4,946,795 A | 8/1990 | Gibbons et al. |
| 5,039,617 A | 8/1991 | McDonald et al. |
| 5,061,381 A | 10/1991 | Burd |
| 5,089,229 A | 2/1992 | Heidt et al. |
| 5,104,813 A | 4/1992 | Besemer et al. |
| 5,122,284 A | 6/1992 | Braynin et al. |
| 5,130,238 A | 7/1992 | Malek et al. |
| 5,162,237 A | 11/1992 | Messenger et al. |
| 5,173,193 A | 12/1992 | Schembri |
| 5,204,525 A | 4/1993 | Hillman et al. |
| 5,242,606 A | 9/1993 | Braynin et al. |
| 5,270,184 A | 12/1993 | Walker et al. |
| 5,273,905 A | 12/1993 | Muller et al. |
| 5,279,607 A | 1/1994 | Schentag et al. |
| 5,281,395 A | 1/1994 | Markart et al. |
| 5,310,652 A | 5/1994 | Gelfand et al. |
| 5,322,770 A | 6/1994 | Gelfand |
| 5,380,487 A | 1/1995 | Choperena et al. |
| 5,399,491 A | 3/1995 | Kacian et al. |
| 5,403,415 A | 4/1995 | Schembri |
| 5,443,790 A | 8/1995 | Coeurveille et al. |
| 5,455,166 A | 10/1995 | Walker |
| 5,472,603 A | 12/1995 | Schembri |
| 5,478,750 A | 12/1995 | Bernstein et al. |
| 5,480,784 A | 1/1996 | Kacian et al. |
| 5,527,670 A | 6/1996 | Stanley |
| 5,545,540 A | 8/1996 | Mian |
| 5,554,539 A | 9/1996 | Chadney et al. |
| 5,578,269 A | 11/1996 | Yaremko et al. |
| 5,590,052 A | 12/1996 | Kopf-Sill et al. |
| 5,591,643 A | 1/1997 | Schembri |
| 5,599,411 A | 2/1997 | Schembri |
| 5,624,850 A | 4/1997 | Kumar et al. |
| 5,648,211 A | 7/1997 | Fraiser et al. |
| 5,670,375 A | 9/1997 | Seaton et al. |
| 5,674,698 A | 10/1997 | Zarling et al. |
| 5,687,716 A | 11/1997 | Kaufmann et al. |
| 5,693,233 A | 12/1997 | Schembri |
| 5,716,852 A | 2/1998 | Yager et al. |
| 5,744,366 A | 4/1998 | Kricka et al. |
| 5,797,898 A | 8/1998 | Santini et al. |
| 5,801,057 A | 9/1998 | Smart et al. |
| 5,807,375 A | 9/1998 | Gross et al. |
| 5,820,548 A | 10/1998 | Sieben et al. |
| 5,832,296 A | 11/1998 | Wang et al. |
| 5,842,787 A | 12/1998 | Kopf-Sill et al. |
| 5,848,991 A | 12/1998 | Gross et al. |
| 5,854,033 A | 12/1998 | Lizardi |
| 5,863,502 A | 1/1999 | Southgate et al. |
| 5,874,046 A | 2/1999 | Megerle |
| 5,874,214 A | 2/1999 | Nova et al. |
| 5,876,675 A | 3/1999 | Kennedy |
| 5,885,470 A | 3/1999 | Parce et al. |
| 5,891,734 A | 4/1999 | Gill et al. |
| 5,902,549 A | 5/1999 | Mimura et al. |
| 5,939,291 A | 8/1999 | Loewy et al. |
| 5,942,443 A | 8/1999 | Parce et al. |
| 5,961,451 A | 10/1999 | Reber et al. |
| 5,961,923 A | 10/1999 | Nova et al. |
| 5,976,896 A | 11/1999 | Kumar et al. |
| 5,980,830 A | 11/1999 | Savage et al. |
| 6,033,850 A | 3/2000 | Purvis |
| 6,046,056 A | 4/2000 | Parce et al. |
| 6,074,616 A | 6/2000 | Buechler et al. |
| 6,123,861 A | 9/2000 | Santini, Jr. et al. |
| 6,156,181 A | 12/2000 | Parce et al. |
| 6,168,948 B1 | 1/2001 | Anderson et al. |
| 6,174,675 B1 | 1/2001 | Chow et al. |
| 6,176,962 B1 | 1/2001 | Soane et al. |
| 6,200,814 B1 | 3/2001 | Malmqvist et al. |
| 6,204,068 B1 | 3/2001 | Soini et al. |
| 6,214,629 B1 | 4/2001 | Freitag et al. |
| 6,221,677 B1 | 4/2001 | Wu et al. |
| 6,235,531 B1 | 5/2001 | Kopf-Sill et al. |
| 6,245,057 B1 | 6/2001 | Sieben et al. |
| 6,251,639 B1 | 6/2001 | Kurn |
| 6,267,858 B1 | 7/2001 | Parce et al. |
| 6,277,605 B1 | 8/2001 | Wijnhoven et al. |
| 6,299,839 B1 | 10/2001 | Karunaratne et al. |
| 6,319,668 B1 | 11/2001 | Nova et al. |
| 6,333,157 B1 | 12/2001 | Miller-Jones et al. |
| 6,340,588 B1 | 1/2002 | Nova et al. |
| 6,352,854 B1 | 3/2002 | Nova et al. |
| 6,361,958 B1 | 3/2002 | Shieh et al. |
| 6,368,275 B1 | 4/2002 | Sliwa et al. |
| 6,368,871 B1 | 4/2002 | Christel et al. |
| 6,369,893 B1 | 4/2002 | Christel et al. |
| 6,372,428 B1 | 4/2002 | Nova et al. |
| 6,375,469 B1 | 4/2002 | Brown |
| 6,403,338 B1 | 6/2002 | Knapp et al. |
| 6,410,278 B1 | 6/2002 | Notomi et al. |
| 6,429,025 B1 | 8/2002 | Parce et al. |
| 6,440,725 B1 | 8/2002 | Pourahmadi et al. |
| 6,464,687 B1 | 10/2002 | Ishikawa et al. |
| 6,471,916 B1 | 10/2002 | Noblett |
| 6,477,394 B2 | 11/2002 | Rice et al. |
| 6,482,593 B2 | 11/2002 | Walt et al. |

(56) References Cited

U.S. PATENT DOCUMENTS

| | | | |
|---|---|---|---|
| 6,484,104 B2* | 11/2002 | Abraham-Fuchs | G16H 10/40 702/19 |
| 6,491,666 B1 | 12/2002 | Santini, Jr. et al. | |
| 6,503,231 B1 | 1/2003 | Prausnitz et al. | |
| 6,520,326 B2 | 2/2003 | McIvor et al. | |
| 6,527,762 B1 | 3/2003 | Santini, Jr. et al. | |
| 6,542,717 B1 | 4/2003 | Zimmerman et al. | |
| 6,544,732 B1 | 4/2003 | Chee et al. | |
| 6,551,838 B2 | 4/2003 | Santini, Jr. et al. | |
| 6,565,815 B1 | 5/2003 | Chang et al. | |
| 6,591,124 B2 | 7/2003 | Sherman et al. | |
| 6,632,216 B2 | 10/2003 | Houzego et al. | |
| 6,649,358 B1 | 11/2003 | Parce et al. | |
| 6,663,003 B2 | 12/2003 | Johnson et al. | |
| 6,664,104 B2 | 12/2003 | Pourahmadi et al. | |
| 6,703,205 B2 | 3/2004 | Kopf-Sill et al. | |
| 6,743,399 B1 | 6/2004 | Weigl et al. | |
| 6,748,337 B2 | 6/2004 | Wardlaw et al. | |
| 6,752,961 B2 | 6/2004 | Kopf-Sill et al. | |
| 6,789,510 B1 | 9/2004 | Lee | |
| 6,832,296 B2 | 12/2004 | Hooker | |
| 6,849,237 B2 | 2/2005 | Housefield et al. | |
| 6,858,185 B1 | 2/2005 | Kopf-Sill et al. | |
| 6,878,540 B2 | 4/2005 | Pourahmadi et al. | |
| 6,878,755 B2 | 4/2005 | Singh et al. | |
| 6,881,541 B2 | 4/2005 | Petersen et al. | |
| 6,887,202 B2 | 5/2005 | Currie et al. | |
| 6,887,693 B2 | 5/2005 | McMillan et al. | |
| 6,893,879 B2 | 5/2005 | Petersen et al. | |
| 6,915,679 B2 | 7/2005 | Chien et al. | |
| 6,923,764 B2 | 8/2005 | Aceti et al. | |
| 6,927,851 B2 | 8/2005 | Mccaffrey et al. | |
| 6,929,636 B1 | 8/2005 | Von Allen | |
| 6,940,598 B2 | 9/2005 | Christel et al. | |
| 6,942,771 B1 | 9/2005 | Kayyem | |
| 6,946,251 B2 | 9/2005 | Kurn | |
| 6,949,377 B2 | 9/2005 | Ho | |
| 6,966,880 B2 | 11/2005 | Boecker et al. | |
| 6,979,424 B2 | 12/2005 | Northrup et al. | |
| 7,039,453 B2 | 5/2006 | Mullick et al. | |
| 7,052,831 B2 | 5/2006 | Fletcher et al. | |
| 7,105,183 B2 | 9/2006 | Mcgrath | |
| 7,112,444 B2 | 9/2006 | Beebe et al. | |
| 7,135,144 B2 | 11/2006 | Christel et al. | |
| 7,172,897 B2 | 2/2007 | Blackburn et al. | |
| 7,177,767 B2 | 2/2007 | Ostoich et al. | |
| 7,178,386 B1 | 2/2007 | Gamble et al. | |
| 7,188,001 B2 | 3/2007 | Young et al. | |
| 7,201,872 B2 | 4/2007 | Meron | |
| 7,238,323 B2 | 7/2007 | Knapp et al. | |
| 7,255,833 B2 | 8/2007 | Chang et al. | |
| 7,291,497 B2 | 11/2007 | Holmes et al. | |
| 7,459,305 B2 | 12/2008 | Levy | |
| 7,497,997 B2 | 3/2009 | Glezer et al. | |
| 7,569,346 B2 | 8/2009 | Petersen et al. | |
| 7,635,594 B2 | 12/2009 | Holmes et al. | |
| 7,636,667 B2 | 12/2009 | Brown | |
| 7,759,067 B2 | 7/2010 | Andersson et al. | |
| 7,765,069 B2 | 7/2010 | Ostoich et al. | |
| 7,771,658 B2 | 8/2010 | Larsen | |
| 7,807,197 B2 | 10/2010 | Lee et al. | |
| 7,824,890 B2 | 11/2010 | Hoser et al. | |
| 7,887,750 B2 | 2/2011 | Blatt et al. | |
| 7,888,125 B2 | 2/2011 | Gibbons et al. | |
| 7,914,994 B2 | 3/2011 | Petersen et al. | |
| 7,998,411 B2 | 8/2011 | Kopf-Sill et al. | |
| 8,029,733 B2 | 10/2011 | Chang et al. | |
| 8,055,329 B2 | 11/2011 | Kimchy et al. | |
| 8,158,430 B1 | 4/2012 | Roy et al. | |
| 8,202,492 B2 | 6/2012 | Linder et al. | |
| 8,247,176 B2 | 8/2012 | Petersen et al. | |
| 8,263,006 B2 | 9/2012 | Sutherland et al. | |
| 8,283,155 B2 | 10/2012 | Holmes et al. | |
| 8,318,109 B2 | 11/2012 | Saltsman et al. | |
| 8,323,887 B2 | 12/2012 | Webster et al. | |
| 8,380,541 B1 | 2/2013 | Holmes | |
| 8,394,608 B2 | 3/2013 | Ririe et al. | |
| 8,580,559 B2 | 11/2013 | Petersen et al. | |
| 8,592,157 B2 | 11/2013 | Petersen et al. | |
| 8,889,083 B2 | 11/2014 | Ismagilov et al. | |
| 9,156,032 B2 | 10/2015 | Petersen et al. | |
| 9,789,481 B2 | 10/2017 | Petersen et al. | |
| 10,533,994 B2 | 1/2020 | Holmes et al. | |
| 2001/0012612 A1 | 8/2001 | Petersen et al. | |
| 2001/0019831 A1 | 9/2001 | Phillips et al. | |
| 2001/0045355 A1 | 11/2001 | Gephart et al. | |
| 2001/0051340 A1 | 12/2001 | Singh et al. | |
| 2001/0051766 A1 | 12/2001 | Gazdzinski | |
| 2001/0053535 A1 | 12/2001 | Bashir et al. | |
| 2002/0001854 A1 | 1/2002 | Lee | |
| 2002/0019060 A1 | 2/2002 | Petersen et al. | |
| 2002/0025576 A1 | 2/2002 | Northrup et al. | |
| 2002/0034757 A1 | 3/2002 | Cubicciotti | |
| 2002/0039783 A1 | 4/2002 | McMillan et al. | |
| 2002/0042125 A1 | 4/2002 | Petersen et al. | |
| 2002/0045246 A1 | 4/2002 | McMillan et al. | |
| 2002/0052761 A1 | 5/2002 | Fey et al. | |
| 2002/0055094 A1 | 5/2002 | Reece et al. | |
| 2002/0055127 A1 | 5/2002 | Gindilis | |
| 2002/0055167 A1 | 5/2002 | Pourahmadi et al. | |
| 2002/0059030 A1 | 5/2002 | Otworth et al. | |
| 2002/0072733 A1 | 6/2002 | Flaherty | |
| 2002/0092770 A1 | 7/2002 | Hedberg et al. | |
| 2002/0109844 A1 | 8/2002 | Christel et al. | |
| 2002/0110496 A1 | 8/2002 | Samsoondar | |
| 2002/0114739 A1 | 8/2002 | Weigl et al. | |
| 2002/0120183 A1 | 8/2002 | Abraham-Fuchs et al. | |
| 2002/0120187 A1 | 8/2002 | Eiffert et al. | |
| 2002/0132226 A1 | 9/2002 | Nair et al. | |
| 2002/0143437 A1 | 10/2002 | Handique et al. | |
| 2002/0161606 A1 | 10/2002 | Bennett et al. | |
| 2002/0175079 A1 | 11/2002 | Christel et al. | |
| 2002/0187074 A1 | 12/2002 | O'Connor et al. | |
| 2003/0014362 A1 | 1/2003 | Yim | |
| 2003/0017467 A1 | 1/2003 | Hooper et al. | |
| 2003/0040881 A1* | 2/2003 | Steger | G16H 40/40 702/123 |
| 2003/0049833 A1 | 3/2003 | Chen et al. | |
| 2003/0049865 A1 | 3/2003 | Santini et al. | |
| 2003/0061687 A1 | 4/2003 | Hansen et al. | |
| 2003/0069560 A1 | 4/2003 | Adamis et al. | |
| 2003/0073931 A1* | 4/2003 | Boecker | A61B 5/0002 600/573 |
| 2003/0097092 A1 | 5/2003 | Flaherty | |
| 2003/0100822 A1 | 5/2003 | Lew et al. | |
| 2003/0104590 A1 | 6/2003 | Santini et al. | |
| 2003/0112432 A1 | 6/2003 | Yguerabide et al. | |
| 2003/0114735 A1 | 6/2003 | Silver et al. | |
| 2003/0117491 A1 | 6/2003 | Avni et al. | |
| 2003/0143551 A1 | 7/2003 | Cattell | |
| 2003/0148362 A1 | 8/2003 | Luka | |
| 2003/0152492 A1 | 8/2003 | Chang et al. | |
| 2003/0153900 A1 | 8/2003 | Aceti et al. | |
| 2003/0167000 A1 | 9/2003 | Mullick et al. | |
| 2003/0170705 A1 | 9/2003 | Schulman et al. | |
| 2003/0185706 A1 | 10/2003 | Ribi | |
| 2003/0191430 A1 | 10/2003 | D'Andrea et al. | |
| 2003/0207457 A1 | 11/2003 | Kopf-Sill et al. | |
| 2003/0208113 A1 | 11/2003 | Mault et al. | |
| 2003/0208133 A1 | 11/2003 | Mault | |
| 2003/0210607 A1 | 11/2003 | Gilbert et al. | |
| 2003/0211007 A1 | 11/2003 | Maus et al. | |
| 2003/0211618 A1 | 11/2003 | Patel | |
| 2003/0212379 A1 | 11/2003 | Bylund et al. | |
| 2003/0214057 A1 | 11/2003 | Huang | |
| 2004/0005247 A1 | 1/2004 | Karp | |
| 2004/0005582 A1 | 1/2004 | Shipwash | |
| 2004/0014202 A1 | 1/2004 | King et al. | |
| 2004/0033553 A1 | 2/2004 | Littarru et al. | |
| 2004/0047767 A1 | 3/2004 | Bergman et al. | |
| 2004/0053290 A1 | 3/2004 | Terbrueggen et al. | |
| 2004/0058378 A1 | 3/2004 | Kong et al. | |
| 2004/0078145 A1 | 4/2004 | Ostoich et al. | |
| 2004/0086872 A1 | 5/2004 | Childers et al. | |

(56) References Cited

U.S. PATENT DOCUMENTS

| | | |
|---|---|---|
| 2004/0096959 A1 | 5/2004 | Stiene et al. |
| 2004/0109793 A1 | 6/2004 | McNeely et al. |
| 2004/0121305 A1 | 6/2004 | Wiegand et al. |
| 2004/0122486 A1 | 6/2004 | Stahmann et al. |
| 2004/0122559 A1 | 6/2004 | Young et al. |
| 2004/0132220 A1 | 7/2004 | Fish |
| 2004/0157336 A1 | 8/2004 | Petroff et al. |
| 2004/0209374 A1 | 10/2004 | Kopf-Sill et al. |
| 2004/0213825 A1 | 10/2004 | Levy |
| 2004/0228766 A1 | 11/2004 | Witty et al. |
| 2004/0260204 A1 | 12/2004 | Boecker et al. |
| 2005/0009101 A1 | 1/2005 | Blackburn |
| 2005/0009191 A1 | 1/2005 | Swenson et al. |
| 2005/0019836 A1 | 1/2005 | Vogel et al. |
| 2005/0054078 A1 | 3/2005 | Miller et al. |
| 2005/0064529 A1 | 3/2005 | Kwon |
| 2005/0090726 A1 | 4/2005 | Ackerman |
| 2005/0100937 A1 | 5/2005 | Holmes |
| 2005/0106713 A1 | 5/2005 | Phan et al. |
| 2005/0112544 A1 | 5/2005 | Xu et al. |
| 2005/0130292 A1 | 6/2005 | Ahn et al. |
| 2005/0130321 A1 | 6/2005 | Nicholson et al. |
| 2005/0136548 A1 | 6/2005 | McDevitt et al. |
| 2005/0137481 A1 | 6/2005 | Sheard et al. |
| 2005/0147559 A1 | 7/2005 | Von Allen |
| 2005/0159982 A1 | 7/2005 | Showalter et al. |
| 2005/0180891 A1 | 8/2005 | Webster et al. |
| 2005/0194316 A1 | 9/2005 | Pourahmadi et al. |
| 2005/0201892 A1 | 9/2005 | Taguchi et al. |
| 2005/0209565 A1 | 9/2005 | Yuzhakov et al. |
| 2005/0221281 A1 | 10/2005 | Ho |
| 2005/0249633 A1 | 11/2005 | Blatt et al. |
| 2005/0255001 A1 | 11/2005 | Padmanabhan et al. |
| 2005/0255600 A1 | 11/2005 | Padmanabhan et al. |
| 2005/0283318 A1 | 12/2005 | Ostoich et al. |
| 2006/0019319 A1 | 1/2006 | Billadeau et al. |
| 2006/0029924 A1 | 2/2006 | Brewster et al. |
| 2006/0062852 A1 | 3/2006 | Holmes |
| 2006/0078998 A1 | 4/2006 | Puskas et al. |
| 2006/0106316 A1 | 5/2006 | Palti |
| 2006/0160205 A1 | 7/2006 | Blackburn et al. |
| 2006/0177873 A1 | 8/2006 | Dowd et al. |
| 2006/0182738 A1 | 8/2006 | Holmes |
| 2006/0211933 A1 | 9/2006 | Zimmermann et al. |
| 2006/0257941 A1 | 11/2006 | Mcdevitt et al. |
| 2006/0264779 A1 | 11/2006 | Kemp et al. |
| 2006/0264780 A1 | 11/2006 | Holmes et al. |
| 2006/0264781 A1 | 11/2006 | Gibbons et al. |
| 2006/0264782 A1 | 11/2006 | Holmes et al. |
| 2006/0264783 A1 | 11/2006 | Holmes et al. |
| 2006/0292039 A1 | 12/2006 | Iida |
| 2007/0059196 A1 | 3/2007 | Brister et al. |
| 2007/0054270 A1 | 5/2007 | Inganas et al. |
| 2007/0118399 A1 | 5/2007 | Avinash et al. |
| 2007/0166195 A1 | 7/2007 | Padmanabhan et al. |
| 2007/0172388 A1* | 7/2007 | Padmanabhan ... B01L 3/502715 422/400 |
| 2007/0224084 A1 | 9/2007 | Holmes et al. |
| 2007/0264629 A1 | 11/2007 | Holmes et al. |
| 2008/0009766 A1 | 1/2008 | Holmes et al. |
| 2008/0057572 A1 | 3/2008 | Petersen et al. |
| 2008/0065420 A1 | 3/2008 | Tirinato et al. |
| 2008/0113391 A1 | 5/2008 | Gibbons et al. |
| 2008/0254532 A1 | 10/2008 | Chang et al. |
| 2009/0093970 A1 | 4/2009 | Lewy et al. |
| 2009/0246782 A1 | 10/2009 | Kelso et al. |
| 2009/0318775 A1 | 12/2009 | Michelson et al. |
| 2010/0068706 A1 | 3/2010 | Pourahmadi et al. |
| 2010/0074799 A1 | 3/2010 | Kemp et al. |
| 2010/0081144 A1 | 4/2010 | Holmes et al. |
| 2010/0081894 A1 | 4/2010 | Zdeblick et al. |
| 2010/0152885 A1 | 6/2010 | Regan et al. |
| 2010/0184093 A1 | 7/2010 | Donovan et al. |
| 2010/0248277 A1 | 9/2010 | Gibbons et al. |
| 2011/0003699 A1 | 1/2011 | Yoder et al. |
| 2011/0104826 A1 | 5/2011 | Gibbons et al. |
| 2011/0166553 A1 | 7/2011 | Holmes et al. |
| 2011/0213564 A1 | 9/2011 | Henke |
| 2011/0213579 A1 | 9/2011 | Henke |
| 2011/0213619 A1 | 9/2011 | Henke |
| 2012/0034598 A1 | 2/2012 | Holmes et al. |
| 2012/0142020 A1 | 6/2012 | Miller |
| 2012/0171758 A1 | 7/2012 | Petersen et al. |
| 2012/0252005 A1 | 10/2012 | Chiang et al. |
| 2012/0258472 A1 | 10/2012 | Roy et al. |
| 2012/0295269 A1 | 11/2012 | Pourahmadi et al. |
| 2013/0080071 A1 | 3/2013 | Holmes |
| 2013/0115685 A1 | 5/2013 | Holmes et al. |
| 2013/0156286 A1 | 6/2013 | Holmes |
| 2013/0220931 A1 | 8/2013 | Petersen et al. |
| 2013/0236907 A1 | 9/2013 | Petersen et al. |
| 2014/0057255 A1 | 2/2014 | Holmes |
| 2014/0141424 A1 | 5/2014 | Pourahmadi et al. |
| 2014/0222447 A1 | 8/2014 | Holmes et al. |
| 2014/0329259 A1 | 11/2014 | Holmes et al. |
| 2014/0335505 A1 | 11/2014 | Holmes |
| 2018/0111123 A1 | 4/2018 | Chatterjee et al. |

FOREIGN PATENT DOCUMENTS

| | | |
|---|---|---|
| CN | 1253625 A | 5/2000 |
| CN | 1262606 A | 8/2000 |
| CN | 1415964 A | 5/2003 |
| CN | 1416528 A | 5/2003 |
| CN | 2559986 | 7/2003 |
| CN | 2559986 Y | 7/2003 |
| CN | 1499949 A | 5/2004 |
| CN | 1526074 A | 9/2004 |
| CN | 1173776 C | 11/2004 |
| CN | 1572320 A | 2/2005 |
| CN | 1192567 C | 3/2005 |
| CN | 1746675 A | 3/2006 |
| EA | 007146 B1 | 8/2006 |
| EP | 0478319 A1 | 4/1992 |
| EP | 0541340 A2 | 5/1993 |
| EP | 0564254 A1 | 10/1993 |
| EP | 0571225 A2 | 11/1993 |
| EP | 0576602 A1 | 1/1994 |
| EP | 0631137 A2 | 12/1994 |
| EP | 0636685 A2 | 2/1995 |
| EP | 0637996 A1 | 2/1995 |
| EP | 0637998 A1 | 2/1995 |
| EP | 0639223 A1 | 2/1995 |
| EP | 0640826 A1 | 3/1995 |
| EP | 0640828 A1 | 3/1995 |
| EP | 0652600 A1 | 5/1995 |
| EP | 684315 A1 | 11/1995 |
| EP | 0684315 A1 | 11/1995 |
| EP | 0693560 A2 | 1/1996 |
| EP | 0723146 A1 | 7/1996 |
| EP | 0734017 A1 | 9/1996 |
| EP | 0844475 A2 | 5/1998 |
| EP | 0962773 A1 | 12/1999 |
| EP | 0971039 A2 | 1/2000 |
| EP | 1002229 A1 | 5/2000 |
| EP | 1086719 A1 | 3/2001 |
| EP | 1106244 A2 | 6/2001 |
| EP | 1174078 A2 | 1/2002 |
| EP | 1202057 A2 | 5/2002 |
| EP | 1203959 A1 | 5/2002 |
| EP | 1225442 A2 | 7/2002 |
| EP | 1346686 A2 | 9/2003 |
| EP | 1360931 A1 | 11/2003 |
| EP | 1415788 A1 | 5/2004 |
| EP | 1498067 A | 1/2005 |
| JP | S6247555 A | 3/1987 |
| JP | H0727700 A | 1/1995 |
| JP | H07103959 A | 4/1995 |
| JP | H07120393 A | 5/1995 |
| JP | H07151101 A | 6/1995 |
| JP | H07196314 A | 8/1995 |
| JP | H07304799 A | 11/1995 |
| JP | H08211071 A | 8/1996 |
| JP | H08334505 A | 12/1996 |

(56) References Cited

FOREIGN PATENT DOCUMENTS

| | | |
|---|---|---|
| JP | H0968533 A | 3/1997 |
| JP | H0980021 A | 3/1997 |
| JP | H09113511 A | 5/1997 |
| JP | H09192218 A | 7/1997 |
| JP | H09244055 A | 9/1997 |
| JP | H09253056 A | 9/1997 |
| JP | H09281078 A | 10/1997 |
| JP | H1072628 A | 3/1998 |
| JP | H10132712 A | 5/1998 |
| JP | H10239240 A | 9/1998 |
| JP | H10267888 A | 10/1998 |
| JP | H10305016 A | 11/1998 |
| JP | H1157560 A | 3/1999 |
| JP | H11352094 A | 12/1999 |
| JP | 2000314719 A | 11/2000 |
| JP | 2001065458 A | 3/2001 |
| JP | 2001157855 A | 6/2001 |
| JP | 2001165752 A | 6/2001 |
| JP | 2001319560 A | 11/2001 |
| JP | 2002010990 A | 1/2002 |
| JP | 2002031055 A | 1/2002 |
| JP | 2002041654 A | 2/2002 |
| JP | 2002044007 A | 2/2002 |
| JP | 2002511965 A | 4/2002 |
| JP | 2002161856 A | 6/2002 |
| JP | 2002263185 A | 9/2002 |
| JP | 2002266762 A | 9/2002 |
| JP | 2002282217 A | 10/2002 |
| JP | 2002538440 A | 11/2002 |
| JP | 2002371955 A | 12/2002 |
| JP | 2003057244 A | 2/2003 |
| JP | 2003504618 A | 2/2003 |
| JP | 2003166910 A | 6/2003 |
| JP | 2003167960 A | 6/2003 |
| JP | 2003207454 A | 7/2003 |
| JP | 2003222611 A | 8/2003 |
| JP | 2003315348 A | 11/2003 |
| JP | 2003322653 A | 11/2003 |
| JP | 2003329696 A | 11/2003 |
| JP | 2004028589 A | 1/2004 |
| JP | 2004101381 A | 4/2004 |
| JP | 2004527825 A | 9/2004 |
| JP | 2004317498 A | 11/2004 |
| JP | 2004333452 A | 11/2004 |
| JP | 2004358261 A | 12/2004 |
| JP | 2005010179 A | 1/2005 |
| JP | 2005015243 A | 1/2005 |
| JP | 2005030983 A | 2/2005 |
| JP | 2005104750 A | 4/2005 |
| JP | 2005130855 A | 5/2005 |
| JP | 2005140681 A | 6/2005 |
| JP | 2005291954 A | 10/2005 |
| JP | 2007187677 A | 7/2007 |
| WO | 9013668 A1 | 11/1990 |
| WO | 9401165 A | 1/1994 |
| WO | 0049176 A1 | 8/2000 |
| WO | WO 00/78454 A1 | 12/2000 |
| WO | WO 01/13127 A1 | 2/2001 |
| WO | 0135928 A | 5/2001 |
| WO | 0164344 A2 | 9/2001 |
| WO | WO 02/064038 A2 | 8/2002 |
| WO | WO 02/064826 A2 | 8/2002 |
| WO | 02064038 A | 8/2003 |
| WO | 03066128 A | 8/2003 |
| WO | 2005024437 A1 | 3/2005 |
| WO | 2005025413 A2 | 3/2005 |
| WO | 2005031355 A | 4/2005 |
| WO | 2005065157 A | 7/2005 |
| WO | 2005065538 A2 | 7/2005 |
| WO | WO2005074161 A1 | 8/2005 |
| WO | 2005121367 A | 12/2005 |
| WO | 2006121510 A2 | 11/2006 |
| WO | WO 2007/092713 A2 | 8/2007 |
| WO | 2007120904 A | 10/2007 |
| WO | 2009046227 A1 | 4/2009 |
| WO | 2011106512 A | 9/2011 |
| WO | 2012040641 A | 3/2012 |
| WO | 2013043204 A1 | 3/2013 |

OTHER PUBLICATIONS

Office Action dated Jun. 1, 2007 for U.S. Appl. No. 11/389,409.
Office Action dated Jun. 1, 2012 for U.S. Appl. No. 11/388,823.
Office Action dated Jun. 11, 2012 for U.S. Appl. No. 11/388,415.
Office Action dated Jun. 11, 2014 for U.S. Appl. No. 12/625,430.
Office Action dated Jun. 12, 2014 for U.S. Appl. No. 12/986,954.
Office Action dated Jun. 18, 2012 for U.S. Appl. No. 13/244,951.
Office Action dated Jun. 19, 2015 for U.S. Appl. No. 13/647,325.
Office Action dated Jun. 20, 2012 for U.S. Appl. No. 13/244,946.
Office Action dated Jun. 21, 2007 for U.S. Appl. No. 11/202,231.
Office Action dated Jun. 24, 2013 for U.S. Appl. No. 13/436,568.
Office Action dated Jun. 5, 2013 for U.S. Appl. No. 12/750,518.
Office Action dated Jun. 9, 2010 for U.S. Appl. No. 11/746,535.
Office Action dated Jul. 18, 2012 for U.S. Appl. No. 12/576,197.
Office Action dated Jul. 25, 2008 for U.S. Appl. No. 11/389,409.
Office Action dated Jul. 27, 2011 for U.S. Appl. No. 11/554,509.
Office Action dated Jul. 28, 2009 for U.S. Appl. No. 11/202,206.
Office Action dated Jul. 29, 2011 for U.S. Appl. No. 12/986,954.
Office Action dated Aug. 24, 2010 for U.S. Appl. No. 11/388,415.
Office Action dated Aug. 25, 2014 for U.S. Appl. No. 14/270,618.
Office Action dated Aug. 27, 2010 for U.S. Appl. No. 11/388,823.
Office Action dated Aug. 29, 2008 for U.S. Appl. No. 11/388,823.
Office Action dated Aug. 31, 2011 for U.S. Appl. No. 12/221,816.
Office Action dated Sep. 1, 2005 for U.S. Appl. No. 10/937,872.
Office Action dated Sep. 11, 2008 for U.S. Appl. No. 11/389,409.
Office Action dated Sep. 22, 2011 for U.S. Appl. No. 12/576,197.
Office Action dated Sep. 4, 2013 for U.S. Appl. No. 11/388,823.
Office Action dated Sep. 5, 2008 for U.S. Appl. No. 11/388,723.
Okamatsu, et al. Epitope mapping of H9N2 influenza virus hemagglutinin and neuraminidase molecule. The Japanese Society of Veterinary Science, Journal of Veterinary Medical Science, Presentation Abstracts, 2004, vol. 137, p. 91, DV-05.
Pal, et al. An integrated microfluidic device for influenza and other genetic analyses. Lab Chip. Oct. 2005;5(10):1024-32. Epub Aug. 18, 2005.
Patolsky, et al. Electrical detection of single viruses. Proc Natl Acad Sci USA. Sep. 28, 2004;101(39):14017-22. Epub Sep. 13, 2004.
PCT Application No. PCT/US2014/016593 filed Jul. 16, 2014.
Pescovitz, D. Sniffing out airborne disease. Lab Note: Research from the College of Engineering, University of California, Berkeley, 2004. Available online at http://www.coe.berkeley.edu/labnotes/0904/pisano.html. Accessed Jan. 28, 2011.
Preininger, et al. Polymer-coated optical fibres for application in a direct evanescent wave immunoassay. Analytica Chimica Acta, 2000; 403; 67-76.
Rai-Choudhury, ed., Handbook of Microlithography, Micromachining & Microfabrication. SPIE Optical Engineering Press. Bellingham, Wash. 1997. (Cover pages and table of contents only).
Ray, et al. Distinct hemagglutinin and neuraminidase epitopes involved in antigenic variation of recent human parainfluenza virus type 2 isolates. Virus Res. Jun. 1992;24(1):107-13.
Red Herring. Stopping bad reactions. Red Herring. Dec. 26, 2005.
Runyan, et al. Semiconductor integrated circuit processing technology. Addison-Wesley Publishing Co., Reading Mass. 1990. (Cover pages and table of contents only).
Sambrook, et al. Molecular Cloning: A Laboratory Manual. Cold Spring Harbor Laboratory Press. New York. 2001. (Cover pages and table of contents only).
Sapsford, et al. Demonstration of four immunoassay formats using the array biosensor. Anal Chem. 2002; 74(5):1061-8.
Scheurle, et al. HER-2/neu expression in archival non-small cell lung carcinomas using FDA-approved hercep test. Anticancer Res. 2000; 20:2091-2096.
Spira, et al. The identification of monoclonal class switch variants by sib selection and an ELISA assay. J Immunol Methods. 1984;74(2):307-15.

(56) References Cited

OTHER PUBLICATIONS

Steplewski, et al. Isolation and characterization of anti-monosialoganglioside monoclonal antibody 19-9 class-switch variants. Proc Natl Acad Sci U S A. 1985; 82(24):8653-7.
Stevens, et al. Glycan microarray analysis of the hemagglutinins from modem and pandemic influenza viruses reveals different receptor specificities. J Mol Biol. Feb. 3, 2006;355(5):1143-55.
Tautz. Hypervariability of simple sequences as a general source for polymorphic DNA markers. Nucleic Acids Res. Aug. 25, 1989;17(16):6463-71.
Tedeschi, et al. Antibody immobilisation on fibre optic TIRF sensors. Biosens Bioelectron. 2003; 19(2):85-93.
U.S. Appl. No. 13/286,168, filed Oct. 31, 2011. Inventors: Holmes et al.
U.S. Appl. No. 13/366,193, filed Feb. 3, 2012. Inventors: Holmes et al.
U.S. Appl. No. 13/629,577, filed Sep. 27, 2012. Inventors: Holmes et al.
U.S. Appl. No. 13/896,171, filed May 16, 2013. Inventors: Holmes, et al.
U.S. Appl. No. 14/050,235, filed Oct. 9, 2013. Inventors: Holmes, et al.
Weber, et al. Abundant class of human DNA polymorphisms which can be typed using the polymerase chain reaction. Am J Hum Genet. Mar. 1989;44(3):388-96.
Williams, et al. DNA polymorphisms amplified by arbitrary primers are useful as genetic markers. Nucleic Acids Res. Nov. 25, 1990;18(22):6531-5.
Yan, et al. Multiplexed flow cytometric immunoassay for influenza virus detection and differentiation. Anal Chem. Dec. 1, 2005;77(23):7673-8.
Zhao, et al. Phylogenetic distribution and genetic mapping of a (GGC)n microsatellite from rice (*Oryza saliva* L.). Plant Mol Biol. Feb. 1993;21(4):607-14.
Zietkiewicz, et al. Genome fingerprinting by simple sequence repeat (SSR)-anchored polymerase chain reaction amplification. Genomics. Mar. 15, 1994;20(2):176-83.
Office Action dated Jan. 12, 2016 for U.S. Appl. No. 13/647,325.
Notice of Allowance dated May 14, 2015 for U.S. Appl. No. 12/625,430.
Notice of Allowance dated Jul. 23, 2015 for U.S. Appl. No. 14/270,618.
Notice of Allowance dated Sep. 2, 2015 for U.S. Appl. No. 12/986,954.
Office Action dated Jan. 11, 2012 for U.S. Appl. No. 13/244,951.
Office Action dated Jan. 13, 2015 for U.S. Appl. No. 13/647,325.
Office Action dated Jan. 16, 2014 for U.S. Appl. No. 13/647,325.
Office Action dated Jan. 27, 2012 for U.S. Appl. No. 13/244,946.
Office Action dated Jan. 5, 2010 for U.S. Appl. No. 11/388,415.
Office Action dated Jan. 8, 2013 for U.S. Appl. No. 11/388,415.
Office Action dated Oct. 17, 2008 for U.S. Appl. No. 11/389,410.
Office Action dated Oct. 26, 2006 for U.S. Appl. No. 10/937,872.
Office Action dated Oct. 31, 2013 for U.S. Appl. No. 12/986,954.
Office Action dated Oct. 6, 2008 for U.S. Appl. No. 11/746,535.
Office Action dated Nov. 22, 2011 for U.S. Appl. No. 11/202,231.
Office Action dated Nov. 5, 2009 for U.S. Appl. No. 11/202,231.
Office Action dated Nov. 9, 2011 for U.S. Appl. No. 11/388,823.
Office Action dated Dec. 11, 2012 for U.S. Appl. No. 12/750,518.
Office Action dated Dec. 19, 2008 for U.S. Appl. No. 11/202,206.
Office Action dated Dec. 22, 2009 for U.S. Appl. No. 11/388,823.
Office Action dated Dec. 22, 2010 for U.S. Appl. No. 11/554,509.
Office Action dated Dec. 3, 2014 for U.S. Appl. No. 12/625,430.
Office Action dated Dec. 9, 2013 for U.S. Appl. No. 12/625,430.
Office Action dated Feb. 1, 2013 for U.S. Appl. No. 13/187,960.
Office Action dated Feb. 17, 2009 for U.S. Appl. No. 11/202,231.
Office Action dated Feb. 2, 2011 for U.S. Appl. No. 11/746,535.
Office Action dated Feb. 22, 2008 for U.S. Appl. No. 11/202,231.
Office Action dated Feb. 22, 2008 for U.S. Appl. No. 11/746,535.
Office Action dated Feb. 27, 2009 for U.S. Appl. No. 11/388,723.
Office Action dated Feb. 9, 2015 for U.S. Appl. No. 12/986,954.
Office Action dated Mar. 16, 2011 for U.S. Appl. No. 11/202,231.
Office Action dated Mar. 17, 2009 for U.S. Appl. No. 11/388,415.
Office Action dated Mar. 18, 2008 for U.S. Appl. No. 11/202,206.
Office Action dated Mar. 21, 2008 for U.S. Appl. No. 11/388,723.
Office Action dated Mar. 21, 2011 for U.S. Appl. No. 11/388,415.
Office Action dated Mar. 22, 2010 for U.S. Appl. No. 11/202,206.
Office Action dated Mar. 25, 2015 for U.S. Appl. No. 14/270,618.
Office Action dated Mar. 3, 2011 for U.S. Appl. No. 11/202,206.
Office Action dated Mar. 5, 2009 for U.S. Appl. No. 11/388,823.
Office Action dated Mar. 5, 2010 for U.S. Appl. No. 11/746,535.
Office Action dated Mar. 7, 2006 for U.S. Appl. No. 10/937,872.
Office Action dated Apr. 1, 2010 for U.S. Appl. No. 11/388,824.
Office Action dated Apr. 13, 2012 for U.S. Appl. No. 11/554,509.
Office Action dated Apr. 18, 2007 for U.S. Appl. No. 10/937,872.
Office Action dated Apr. 29, 2009 for U.S. Appl. No. 11/389,409.
Office Action dated Apr. 30, 2009 for U.S. Appl. No. 11/388,824.
Office Action dated Apr. 30, 2013 for U.S. Appl. No. 13/647,325.
Office Action dated Apr. 4, 2013 for U.S. Appl. No. 12/986,954.
Office Action dated Apr. 5, 2010 for U.S. Appl. No. 11/554,509.
Office Action dated Apr. 8, 2009 for U.S. Appl. No. 11/389,410.
Office Action dated May 22, 2009 for U.S. Appl. No. 11/746,535.
Abbott. FDA Clears Abbott's i-STAT 1 Wireless Point of Care Testing System. Press release dated Mar. 29, 2011.
Abbott. Procedure Manual for the i-STAT System. Rev. dated Jul. 12, 2004.
Abbott. Testing Cartridges for the i-STAT System. Rev. B. Jun. 2009. Available at http://www.abbottpointofcare.com/PDFs/17845_CrtrdgeBrochure_M1.pdf. Accessed Sep. 13, 2011.
Bawendi, et al. The quantum-mechanics of larger semiconductor clusters. Annu. Rev. Phys. Chem. 1990; 41:477-496.
BD Biosciences, Directigen FluA&B Assay Manual. Oct. 11, 2016, pp. 1-11.
Beier, et al. Versatile derivatisation of solid support media for covalent bonding on DNA-microchips. Nucleic Acids Res. 1999; 27:1970-1977.
Bes, et al. Mapping the paratope of anti-CD4 recombinant Fab 13B8.2 by combining parallel peptide synthesis and site-directed mutagenesis. J Biol Chem. Apr. 18, 2003;278(16):14265-73.
Bhatia, et al. Use of thiol-terminal silanes and heterobifuntional crosslinkers for immobilization of antibodies on silica surfaces. Anal Biochem. 1989; 178(2):408-13.
Botstein, et al. Construction of a genetic linkage map in man using restriction fragment length polymorphisms. Am J Hum Genet. May 1980;32(3):314-31.
Broadcaster Moira Gunn with Elizabeth Holmes, recorded Mar. 5, 2005 on Biotech Nation.
Bruchez, et al. Semiconductor nanocrystals as fluorescent biological labels. Science. 1998; 281(5385):2013-6.
Celebre, et al. A comparative sudy of efficiencies of fibre optic and prism TIRF sensors. Meas. Sci. Technol. 1992; 3:1166-1173.
Chan. Quantum dot bioconjugates for ultrasensitive nonisotopic detection. Science. 1998;281(5385):2016-8.
Chang, et al. Micromachining & Microfabrication. SPIE Optical Engineering Press. Bellingham, Wash. 1997. (Cover pages and table of contents only).
Charles, et al. Synthesis of a flurescent analog of polychlorinated biphenyls for use in a continuous flow immunosensor assay. Bioconjug Chem. 1995; 6(6):691-4.
Di Serio, et al. Integration between the tele-cardiology unit and the central laboratory: methodological and clinical evaluation of point-of-care testing cardiac marker in the ambulance. Clin Chem Lab Med. 2006;44(6):768-73.
Duffy, et al. Rapid Prototyping of Microfluidic Systems in Poly(dimethylsiloxane). Analytical Chemistry. 1998; 70(23);4974-4084.
European search report and search opinion dated Feb. 7, 2012 for EP Application No. 11180769.9.
European search report and search opinion dated Mar. 6, 2012 for EP Application No. 10179887.4.
European search report and search opinion dated May 29, 2012 for EP Application No. 11180769.9.
European search report dated Jun. 2, 2009 for Application No. 07762092.

(56) References Cited

OTHER PUBLICATIONS

Gavin, et al. Review of Rapid Diagnostic Tests for Influenza. Clinical and Applied Immunology Reviews. 2004; 4(3):151-172.
Geddes, et al. The impedance of stainless-steel electrodes. Med Biol Eng. Sep. 1971;9(5):511-21.
Guatelli, et al. Isothermal, in vitro amplification of nucleic acids by a multienzyme reaction modeled after retroviral replication. Proc. Natl. Acad. Sci. USA. 1990;87:1874-1878.
Harlow, et al. Antibodies: A Laboratory Manual. Cold Spring Harbor Laboratory. New York. 1988. (Cover pages and table of contents only).
Harrison's Principles of Internal Medicine, Part 2 Cardinal Manifestations of Disease, Ch. 60 (12th ed. 1991; pp. 338-343.).
Health Buddy device. Available at http://www.3hc.org/images/2009%20images/health-buddy-appliance.gif. Accessed Aug. 26, 2011.
Health Buddy Health Management Programs. Available at http://www.bosch-telehealth.com/content/language1/img_zoom/health_buddy_system_gif. Accessed Aug. 26, 2011.
Hirsh, et al. The electrical conductivity of blood. I: Relationship to erythrocyte concentration. Blood. Nov. 1950;5(11):1017-35.
International search report and written opinion dated Jan. 18, 2012 for PCT/US2011/053189.
International Search Report and Written Opinion dated Jul. 16, 2014 for PCT/US2014/016593.
International search report and written opinion dated Sep. 16, 2008 for PCT/US2007/009878.
International search report dated Jan. 22, 2008 for PCT/US06/42563.
International search report dated Dec. 8, 2008 for PCT/US06/11090.
International search report dated Jul. 4, 2005 for PCT/US04/029462.
International search report dated Aug. 11, 2008 for PCT/US07/68665.
International search report dated Sep. 9, 2008 for PCT/US07/23904.
Jaeger. Introduction to Microelectronic fabrication. Addison-Wesley Publishing Co. Reading Mass. 1988. (Cover pages and table of Contents only).
Janet Rehnquist. Enrollment and Certification Processes in the Clinical Laboratory Improvement Amendments Program.
Kessler, et al. Use of the DNA flow-thru chip, a three-dimensional biochip, for typing and subtyping of influenza viruses. J Clin Microbiol. May 2004;42(5):2173-85.
Khan, et al. Detection of influenza virus neuraminidase-specific antibodies by an enzyme-linked immunosorbent assay. J Clin Microbiol. Jul. 1982;16(1): 115-22.
Kilbourne, et al. Independent and disparate evolution in nature of influenza A virus hemagglutinin and neuraminidase glycoproteins. Proc Natl Acad Sci U S A. Jan. 1990;87(2):786-90.
Kwok, et al. Increasing the information content of STS-based genome maps: identifying polymorphisms in mapped STSs. Genomics. Jan. 1, 1996;31(1):123-6.
Landgren. Molecular mechanics of nucleic acid sequence amplification. Trends Genet. Jun. 1993;9(6):199-204.
Lee, et al. Microfluidic enzyme-linked immunosorbent assay technology. Adv Clin Chem. 2006;42:255-95.
Liu, et al. Validation of a fully integrated microfluidic array device for influenza a subtype identification and sequencing. Anal Chem. Jun. 15, 2006;78(12):4184-93.
Lizardi, et al. Exponential amplification of recombinant-RNA hybridization probes. BioTechnol. 1988; 6:1197-1202.
Lupiani, et al. Improved diagnostic tests for Avian influenza surveillance, 2005. Proceedings of the Institute of Food Technologies' First Annual Farad protection and Defense Research Conference.

Mohapatra, et al. Blood resistivity and its implications for the calculation of cardic output by the thoracic electrical impedance technique. Intensive Care Med. Aug. 1977;3(2):63-7.
Mukerjee, et al. Microneedle array for transdermal biological fluid extraction and in situ analysis. Sensors and Actuators A. 2004; 114:267-275.
UnifiedPatents blog post dated May 7, 2020, available at https://www.unifiedpatents.com/insights/2020/5/7/1/prior-art-theranos-covid.
UnifiedPatents Patroll Winning Submission; (Holmes I), linked to UnifiedPatents blog post dated May 7, 2020.
UnifiedPatents Patroll Winning Submission; (Holmes II), linked to UnifiedPatents blog post dated May 7, 2020.
Apex Standards Enterprise; Pseudo Claim Charting; US10533994B2, linked to UnifiedPatents blog post dated May 7, 2020.
Apex Standards Enterprise; Pseudo Claim Charting; U.S. Pat. No. 8,283,155B2, linked to UnifiedPatents blog post dated May 7, 2020.
"Products," Cepheid, Inc., Sunnyvale, California, United States, https://web.archive.org/web/20040407201033/http://cepheid.com:80/pages/products.html, archived Apr. 7, 2004.
"Cepheid—Products," Cepheid, Inc., Sunnyvale, California, United States, https://web.archive.org/web/2004/0614174818/https://www.cepheid.com:80/Sites/cepheid/content.cfm?id=158, archived Jun. 14, 2004.
Belgrader, P., et al., "A microfluidic cartridge to prepare spores for PCR analysis," Biosensors & Bioelectronics, vol. 14: 849-852 (2000).
Ulrich, M. P., et al., "Evaluation of the Cepheid GeneXpert® system for detecting Bacillu antracis," Journal of Applied Microbiology, vol. 100: 1011-1016 (2006).
McMillan, W. A., "Real-time point-of-care molecular detection of infectious disease agents," American Clinical Laboratory, vol. 21(1): 29-31 (2002).
Meehan, P. J., et al., "Responding to Detection of Aerosolized Bacillus anthracis by Autonomous Detection Systems in the Workplace," Morbidity and Mortality Weekly Report: Recommendations and Reports, vol. 53 (7): 1-12 (2004).
Petersen, K., et al., "IVD systems in bioterrorism response," IVDT: Beyond Clinical Diagnostics, vol. 8(4): 35-40 (2002).
"Cepheid Granted US Patent Covering Key Internal Control Method for Ensuring Accurate DNA Test Results," Cepheid Inc., Sunnyvale, California, United States, Nov. 27, 2001.
Piccolo® Operator's Manual, Abaxis, Inc., Union City, California, United States, Mar. 2001.
von Schenck, H., et al., "Evaluation of "HemoCue," a New Device for Determining Hemoglobin," Clin. Chem., vol. 32(3): 526-529 (1986).
Neufeld, L., et al., "Hemoglobin measured by Hemocue and a reference method in venous and capillary blood: A validation study," Salud Publica de Mexico, vol. 44(3): 219-227 (2002).
HemoCue Hb 201+ Operating Manual, HomeCue AB, Angelholm, Sweden, www.hemocue.com (2001).
Ingands, M., et al., "Integrated Microfluidic Compact Disc Device with Potential Use in Both Centralized and Point-of-Care Laboratory Settings," Clinical Chemistry, vol. 51(10): 1985-1987 (2005).
Cheng, S. B., et al., "Development of a Multichannel Microfluidic Analysis System Employing Affinity Capillary Electrophoresis for Immunoassay," Anal. Chem., vol. 73(7): 1472-1479 (2001).
Clayton, J., "Go with the microflow," Nature Methods, vol. 2(8): 621-627 (2005).
Hong, J. W., et al., "A nanoliter-scale nucleic acid processor with parallel architecture," Nature Biotechnology, vol. 22(4): 435-439 (2004).

\* cited by examiner

Typical assay dose-response data for a two-step assay for TxB2

Dose responses computed with and without errors in calibration parameters.

Computed concentration errors produced by 1% mis-estimation of A and D calibration values Calibration using a "differential" approach Verification of calibration using the "1-point spike" method (log scale)

Verification of calibration using the "1-point spike" method (linear scale)

Dose-response of assays calibrated against a plasma sample with a very low TxB2 concentration Using spike recovery to eliminate calibration errors of the "C" parameter.

Calculating difference in concentration between two samples

Assay of plasma samples

Time course of assay signal generation

Impact of change in calibration parameter A on assay calibration

| Subject | Candidate output parameter | | | | | | Input parameter | | | | | |
|---|---|---|---|---|---|---|---|---|---|---|---|---|
| | OP1 | OP2 | OP3 | . | . | OPn | IP1 | IP2 | IP3 | . | . | IPn |
| 1 | | | | | | | | | | | | |
| 2 | | | | | | | | | | | | |
| 3 | | | | | | | | | | | | |
| . | | | | | | | | | | | | |
| . | | | | | | | | | | | | |
| . | | | | | | | | | | | | |
| N | | | | | | | | | | | | |

Figure 19

Computing the Therapeutic Index (TI)

Multiple Regression Analysis of the Computed TI

Illustration of the relationship between measured drug, analyte and biomarker concentration and therapeutic index.

Illustration of the application of this invention to minimize ADRs.

User Enter Food

Enter Food and Servings

Food Name: peach

Amount: 1  serving

Enter a food.

Date: January 1, 2004

Time: 0 : 00

Set to Now

Submit  Reset Form  Commit  Cancel

Food Values

| Amount | Units | Food | Cal. | Fat | Sat.Fat | Carb | Prot. |
|---|---|---|---|---|---|---|---|
| 1 | sv | Banana | 105 | 0 | 0 | 26 | 1 |
|  |  | Totals | 105 | 0 | 0 | 26 | 1 |

Figure 24

Patient input values

Use of TI to follow treatment progression in an autism patient

CALIBRATION OF FLUIDIC DEVICES

CROSS-REFERENCE

This application is a continuation application of Ser. No. 11/388,824, filed Mar. 24, 2006, which claims the benefit of U.S. Provisional Application No. 60/678,801, filed May 9, 2005, U.S. Provisional Application No. 60/705,489, filed Aug. 5, 2005, U.S. Provisional Application No. 60/717,192, filed Sep. 16, 2005, and U.S. Provisional Application No. 60/721,097, filed Sep. 28, 2005 which are incorporated herein by reference in their entirety.

BACKGROUND OF THE INVENTION

The discovery of a vast number of biomarkers implicated in a wide variety of biological processes and the establishment of miniaturized microfluidic systems have opened up avenues to devise methods and systems for the prediction, diagnosis and treatment of diseases in a point-of-care setting. Point-of-care testing is particularly desirable because it rapidly delivers results to medical practitioners and enables faster consultation.

Performing assays, particularly immunoassays, on microfluidic systems of patient samples requires careful, precise calibration using data gathered in parallel with the sample measurement by measuring known standards or calibrators using the same assay protocol and reagents, or data provided by a manufacturer that are specific to a particular lot of reagents and assay conditions. Generally, such manufacturer provided calibration data are associated with strict temperature and other assay related conditions. Such calibration information is critical in accurately determining the relationship between the response or output from the assay system and the analyte concentration in a sample. Errors due to mis-calibration of distributed assay systems, especially in the case of immunoassays and particularly in the case of immunoassays that do not use "excess" reagents could lead to significant errors in determining the concentration of an analyte of interest.

There is therefore a significant need for methods that would improve the calibration in hand held or disposable assay units, particularly in those units where the sample and/or reagent volumes are in the microliter and nanoliter ranges, where maintaining a controlled temperature may be impractical, where the sample may not be "clean" such that errors are caused by interfering substances, or where it is difficult to maintain the desired conditions such as temperature, reagent quality, or sample volume.

SUMMARY OF THE INVENTION

The present invention provides a method of improving the accuracy of calibrating a fluidic system. The method comprises providing a system for detecting an analyte in a bodily fluid from a subject comprising a fluidic device for providing said bodily fluid, said fluidic device having a calibration assembly and a reader assembly for detecting the presence of said analyte, measuring one or more parameters of a calibration curve associated with said fluidic device, comparing said one or more parameters with predetermined parameters associate with said fluidic device, and adjusting a signal output by the ratio of said one or more parameters and said predetermined parameters.

In one aspect of the method the predetermined parameters are parameters determined at the time the fluidic device is manufactured.

In another aspect of the method the predetermined parameters are replaced with said measured one or more parameters to be used in a calibration curve to scale a signal to determine said analyte concentration.

The present invention provides another method of improving the calibration of a fluidic system. The method comprises measuring a first signal in an original sample comprising a known quantity of an analyte, measuring a second signal after spiking said original sample with a known quantity of said analyte, plotting the difference between said first and second signals against a target value, wherein said target value is a signal expected for said known quantity of said analyte, and arriving at a best fit of parameters by minimizing the sum of the square of the differences between said target value and calculated analyte values.

In one aspect of the method the sample is provided to a fluidic device, the fluidic device comprises a sample collection unit and an assay assembly, wherein said sample collection unit allows a sample of bodily fluids to react with reactants contained within said assay assembly.

The present invention further provides a method of assessing the reliability of an assay for an analyte in a bodily fluid with the use of a fluidic device. The method comprises providing a system, the system comprising a fluidic device, said fluidic device comprising a sample collection unit and an assay assembly, wherein said sample collection unit allows a sample of bodily fluid to react with reactants contained within said assay assembly, for detecting the presence of an analyte in a bodily fluid from a subject, and a reader assembly for detecting the presence of said analyte, and sensing with a sensor a change in operation parameters under which the system normally operates.

One aspect of the method further comprises improving the reliability of said assay by adjusting the operating parameters to effect normal functioning of the system.

In one aspect the sensor is associated with the fluidic device and is capable of communicating the change to the reader assembly.

In some aspects the change is a change in temperature, pressure, or the presence of moisture.

In one aspect the sensor is associated with the reader assembly and is capable of communicating said change to an external device.

One aspect of the method further comprises adjusting a calibration step of said system.

One aspect of the method further comprises wirelessly communicating said change via a handheld device.

Further provided in the present invention is a method of performing a trend analysis on the concentration of an analyte in a subject. The method comprises providing a fluidic device comprising at least one sample collection unit, an immunoassay assembly containing immunoassay reagents, a plurality of channels in fluid communication with said sample collection unit and/or said immunoassay assembly, actuating said fluidic device and directing said immunoassay reagents within said fluidic device, allowing a sample of bodily fluid of less than about 500 ul to react with said immunoassay reagents contained within said assay immunoassay assembly to yield a detectable signal indicative of the presence of said analyte in said sample, detecting said detectable signal generated from said analyte collected in said sample of bodily fluid, and repeating the steps for a single patient over a period of time to detect concentrations of said analyte, thereby performing the trend analysis.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 19 shows how a reference therapeutic index would be computed.

FIG. 24 shows exemplary patient input values.

DETAILED DESCRIPTION OF THE INVENTION

One aspect of the present invention is a system for detecting an analyte in a sample of bodily fluid. In some embodiments a bodily fluid sample is taken from a patient into a fluidic device comprising a sample collection unit, an assay assembly, fluidic channels, and assay reagents. Using an assay, an analyte present in the bodily fluid sample can generate a signal indicative of the presence of the analyte. A reader assembly comprising a detection assembly can then detect the signal. A communications assembly can then transmit the detected signal to an external device for processing. In preferred embodiments, the external device comprises a protocol to run on the fluidic device based on the identification of the fluidic device.

Figure 1:
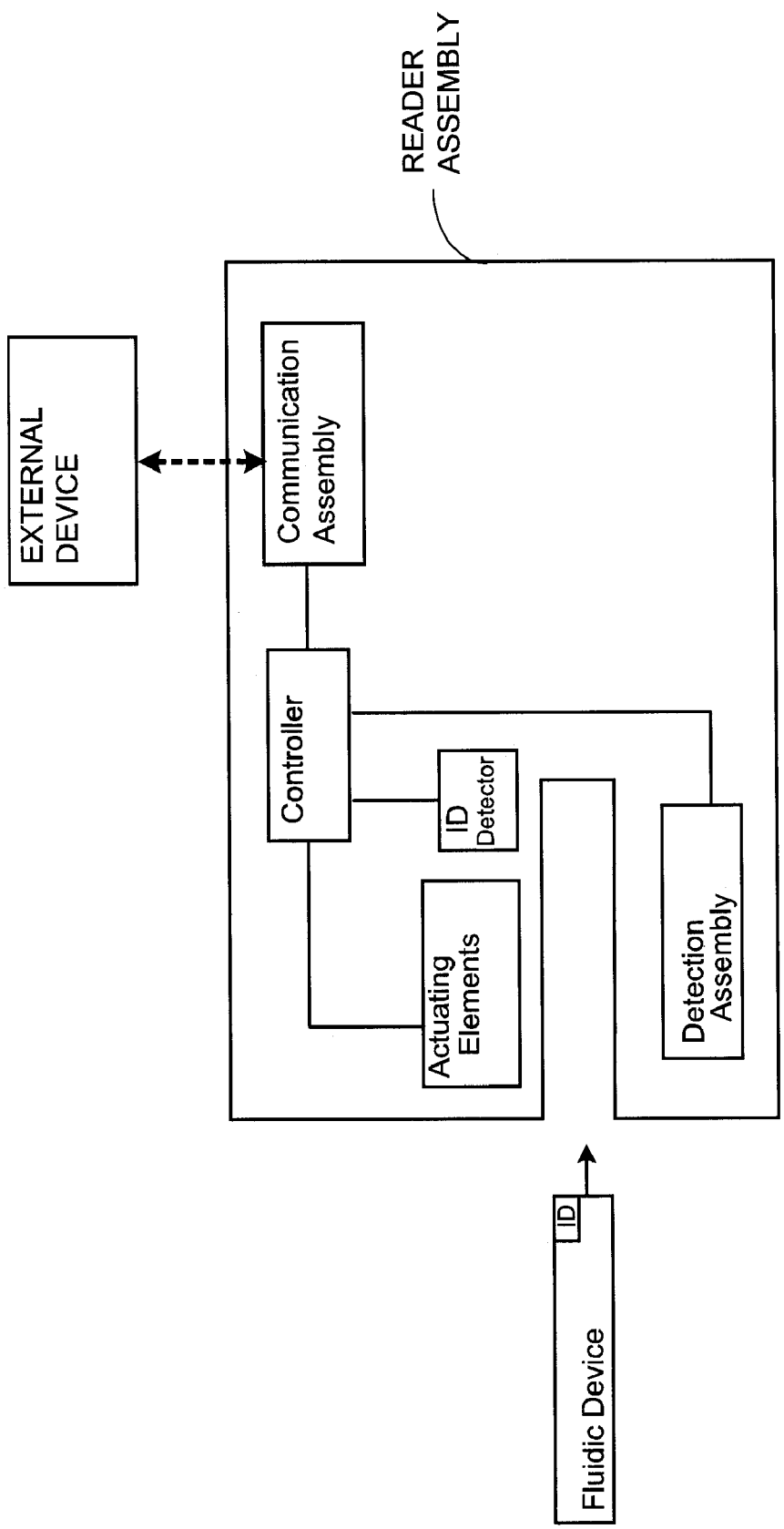
FIG. 1 is an embodiment showing multiple components of the present system.

FIG. 1 illustrates an exemplary system of the present invention. As illustrated, a fluidic device provides a bodily fluid from a patient and can be inserted into a reader assembly. The fluidic device may take a variety of configurations and in some embodiments the fluidic device may be in the form of a cartridge. An identifier (ID) detector may detect an identifier on the fluidic device. The identifier detector communicates with a communication assembly via a controller which transmits the identifier to an external device. The external device sends a protocol stored on the external device to the communication assembly based on the identifier. The protocol to be run on the fluidic device may comprise instructions to the controller of the reader assembly to perform the protocol on the fluidic device, including but not limited to a particular assay to be run and/or a detection method to perform. Once the assay is performed on the fluidic device, a signal indicative of an analyte in the bodily fluid sample may be generated and detected by a detection assembly. The detected signal may then be communicated to the communications assembly, where it can be transmitted to the external device for processing, including without limitation, calculation of the analyte concentration in the sample.

Figure 2:
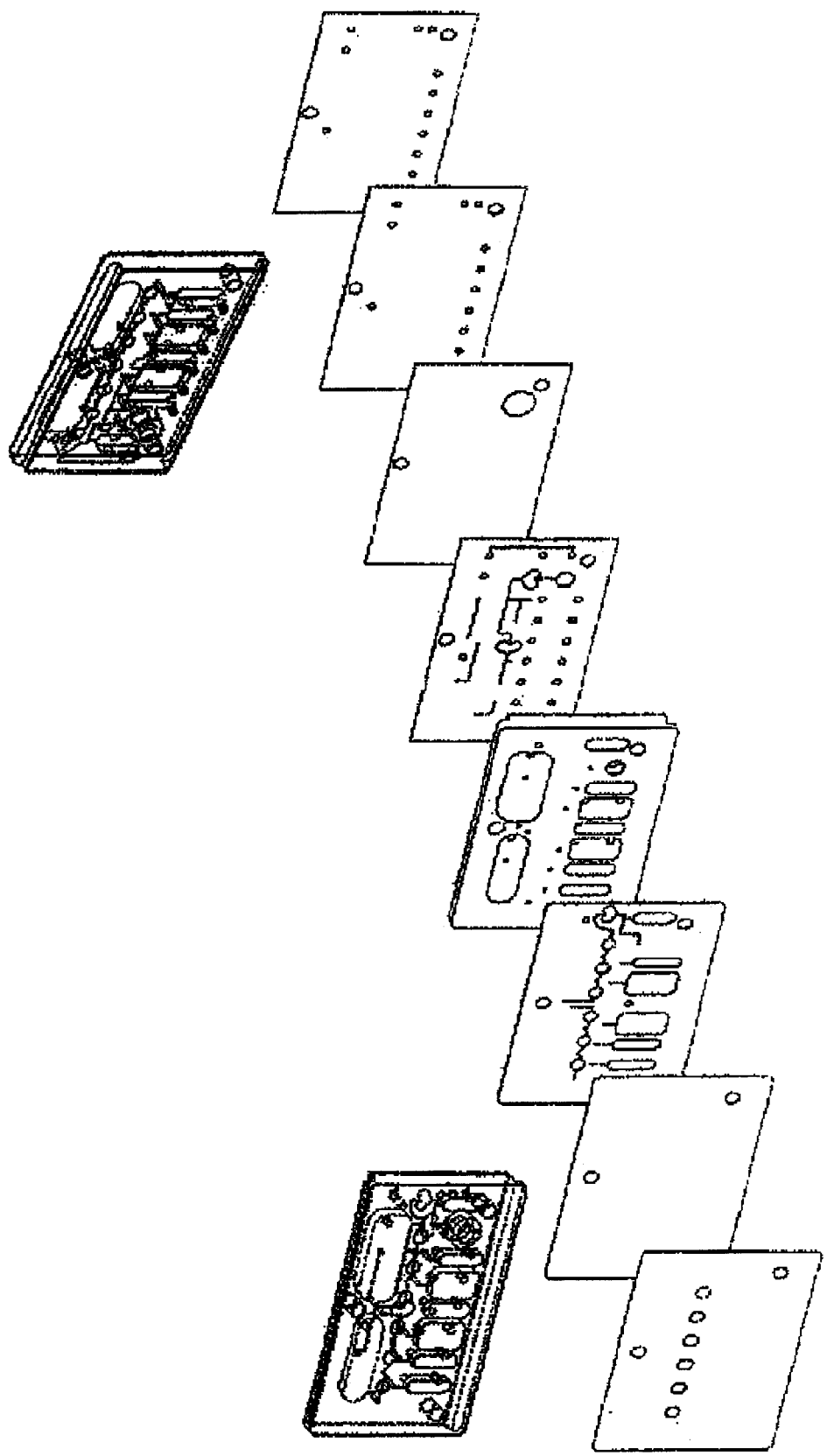
FIG. 2 shows different layers of an exemplary fluidic device prior to assembly.
Figure 3:
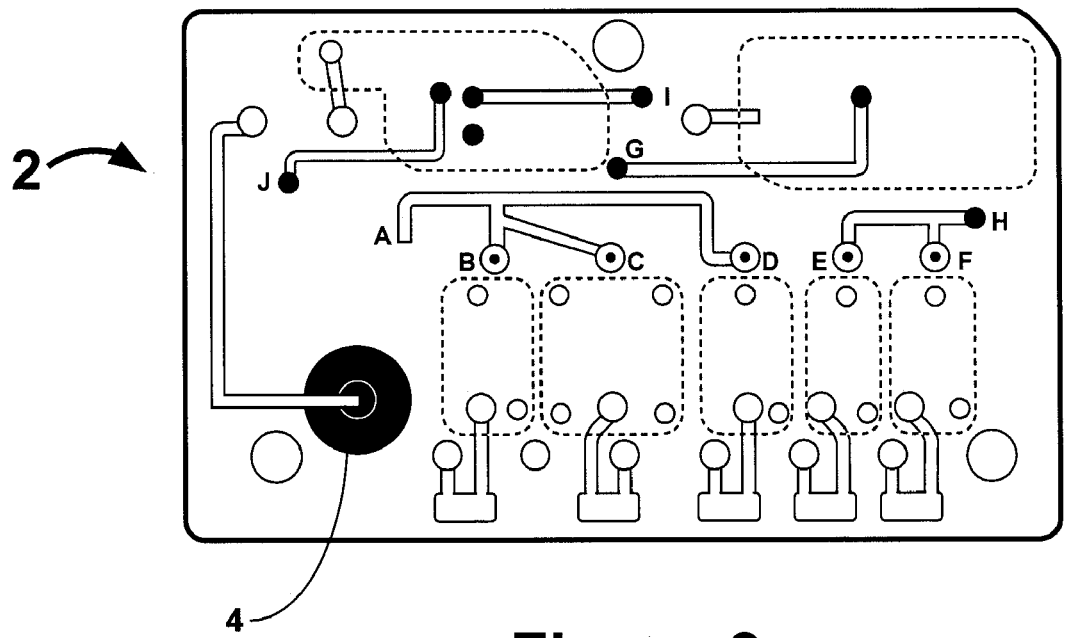
FIGS. 3 and 4 illustrate the fluidic network within an exemplary fluidic device.
Figure 4:
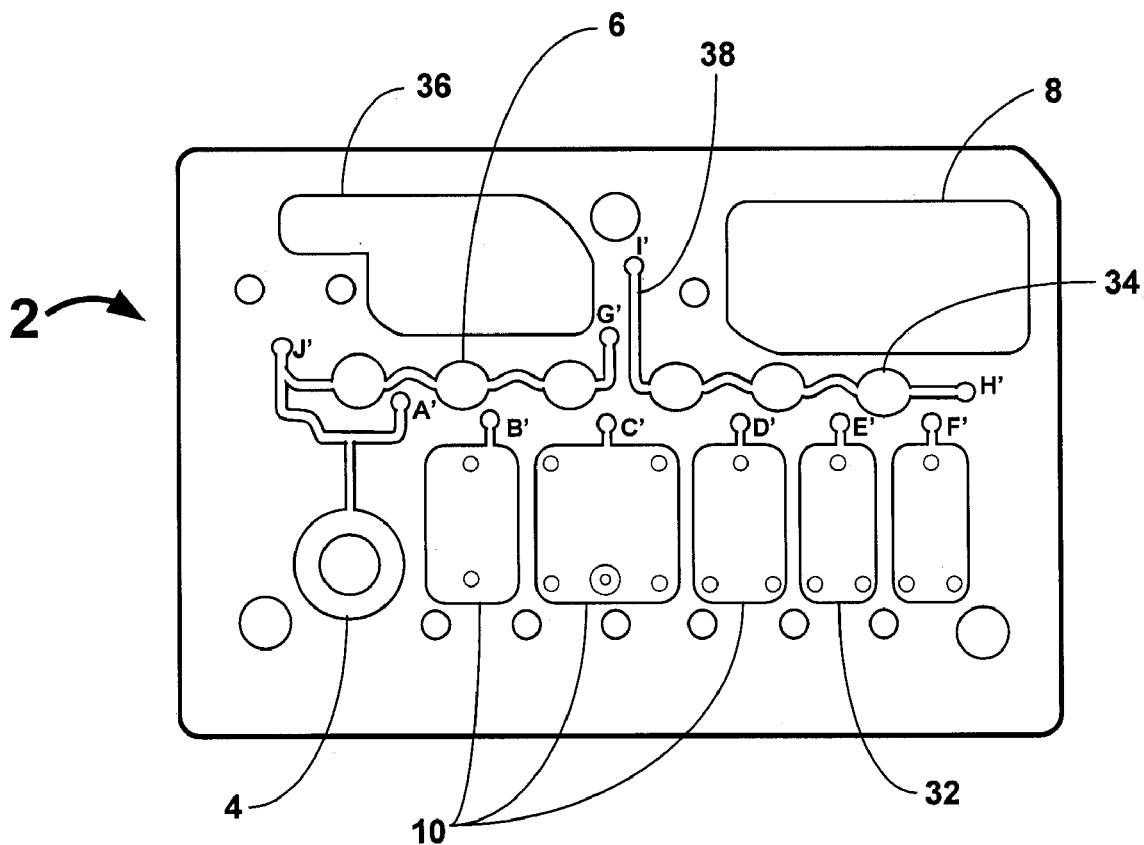

FIG. 2 illustrates exemplary layers of a fluidic device according to the present invention prior to assembly of the fluidic device which is disclosed in more detail below. FIGS. 3 and 4 illustrate the fluidic network of an exemplary fluidic device. The different layers are designed and assembled to form a three dimensional fluidic channel network. A sample collection unit 4 provides a sample of bodily fluid from a patient. As will be explained in further detail below a reader assembly comprises actuating elements (not shown) that can actuate the fluidic device to start and direct the flow of a bodily fluid sample and assay reagents in the fluidic device. In some embodiments actuating elements first cause the flow of sample in the fluidic device 2 from sample collection unit 4 to reaction sites 6, move the sample upward in the fluidic device from point G' to point G, and then to waste chamber 8. The actuating elements then initiate the flow of reagents from reagent chambers 10 to point B', point C', and point D', upward to points B, C, and D, respectively. The reagents then move to point A, down to point A', and then to waste chamber 8 in a manner similar to the sample.

One of the advantages of the present invention is that any reagents necessary to perform an assay on a fluidic device according to the present invention are preferably on-board, or housed within the fluidic device before, during, and after the assay. In this way the only inlet or outlet from the fluidic device is preferably the bodily fluid sample initially provided by the fluidic device. This design also helps create an easily disposable fluidic device where all fluids or liquids remain in the device. The on-board design also prevents leakage from the fluidic device into the reader assembly which should remain free from contamination from the fluidic device.

In a preferred embodiment there is at least one reagent chamber. In some embodiments there may be two, three, four, five, six, or more, or any number of reagent chambers as are necessary to fulfill the purposes of the invention. A reagent chamber is preferably in fluid communication with at least one reaction site, and when the fluidic device is actuated as described herein, reagents contained in said reagent chambers are released into the fluidic channels within the fluidic device.

Reagents according to the present invention include without limitation wash buffers, substrates, dilution buffers, conjugates, enzyme-labeled conjugates, DNA amplifiers, sample diluents, wash solutions, sample pre-treatment reagents including additives such as detergents, polymers, chelating agents, albumin-binding reagents, enzyme inhibitors, enzymes, anticoagulants, red-cell agglutinating agents, antibodies or other materials necessary to run an assay on a fluidic device. An enzyme conjugate can be either a polyclonal antibody or monoclonal antibody labeled with an enzyme, such as alkaline phosphatase or horseradish peroxidase. In some embodiments the reagents are immunoassay reagents.

In some embodiments a reagent chamber contains approximately about 50 µl to about 1 ml of fluid. In some embodiments the chamber may contain about 100 µl of fluid. The volume of liquid in a reagent chamber may vary depending on the type of assay being run or the sample of bodily fluid provided. In some embodiments the reagents are initially stored dry and liquified upon initiation of the assay being run on the fluidic device.

A variety of assays may be performed on a fluidic device according to the present invention to detect an analyte of interest in a sample. Using labels in an assay as a way of detection the concentration of the analyte of interest is well known in the art. In some embodiments labels are detectable by spectroscopic, photochemical, biochemical, immunochemical, or chemical means. For example, useful nucleic acid labels include 32P, 35S, fluorescent dyes, electron-dense reagents, enzymes, biotin, dioxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include radionucleotides, enzymes, substrates, cofactors, inhibitors, fluorescent moieties, chemiluminescent moieties, bioluminescent labels, calorimetric labels, or magnetic particles. Labeling agents optionally include, for example, monoclonal antibodies, polyclonal antibodies, proteins, or other polymers such as affinity matrices, carbohydrates or lipids. Detection proceeds by any of a variety of known methods, including spectrophotometric or optical tracking of radioactive or fluorescent markers, or other methods which track a molecule based upon size, charge or affinity. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Thus, a label includes without limitation any composition detectable by spectroscopic, photochemical, biochemical, immunochemical, electrical, optical, thermal, or chemical means.

In some embodiments assays performed on the fluidic device will generate photons in the reaction sites indicative of the presence of an analyte of interest. To ensure that a given photon count, for example, detected from a reaction site correlates with an accurate concentration of an analyte of interest in a sample, it is preferably advantageous to calibrate the fluidic device before the detection step. Calibrating a fluidic device at the point of manufacturing, for example, may be insufficient to ensure an accurate analyte concentration is determined because a fluidic device may be shipped prior to use and may undergo changes in temperature, for example, so that a calibration performed at manufacturing does not take into effect any subsequent changes to the structure of the fluidic device or reagents contained therein. In a preferred embodiment of the present invention, a fluidic device has a calibration assembly that is similar to the assay assembly in components and design. One difference is that a sample is preferably not introduced into the calibration assembly. Referring to FIGS. 3 and 4, a calibration assembly occupies about half of the fluidic device 2 and includes reagent chamber 32, reactions site 34, a waste chamber 36, and fluidic channel 38. Similar to the assay assembly, the number of reagent chambers and reaction sites may vary depending on the assay being run on the fluidic device and the number of analytes being detected.

An additional method of improving the accuracy of a calculated analyte concentration or pharmacokinetic or pharmacodynamic parameter measured according to the present invention is to provide a sensor on either the fluidic device or reader assembly, or both, that can sense, for example, changes in temperature or pressure that could impact the performance of the present system.

A fluidic device and reader assembly may, after manufacturing, be shipped to the end user, together or individually. As a reader assembly is preferably repeatedly used with multiple fluidic devices, it may be necessary to have sensors on both the fluidic device and reader assembly to detect such changes during shipping, for example. During shipping, pressure or temperature changes can impact the performance of a number of components of the present system, and as such a sensor located on either the fluidic device or reader assembly can relay these changes to, for example, the external device so that adjustments can be made during calibration or during data processing on the external device, or both. For example, if the pressure of a fluidic device dropped to a certain level during shipping, a sensor located on the fluidic device could detect this change and convey this information to the reader assembly when it is inserted into the reader assembly by the user. There may be an additional detection device in the reader assembly to perform this, or such a device may be incorporated into another system component. In some embodiments this information may be wirelessly transmitted to either the reader assembly or the external device. Likewise, a sensor in the reader assembly can detect similar changes. In some embodiments, it may be desirable to have a sensor in the shipping packaging as well, either instead of in the system components or in addition to.

In some embodiments at least one of the different layers of the fluidic device may be constructed of polymeric substrates. Non limiting examples of polymeric materials include polystyrene, polycarbonate, polypropylene, polydimethylsiloxanes (PDMS), polyurethane, polyvinylchloride (PVC), and polysulfone.

In some embodiments the reader assembly comprises an identifier detector for detecting or reading an identifier on the fluidic device, a controller for automatically controlling the detection assembly and also mechanical components of the reader assembly, for example, pumps and/or valves for controlling or directing fluid through the fluidic device, a detection device for detecting a signal created by an assay run on the fluidic device, and a communication assembly for communicating with an external device.

In preferred embodiments the reader assembly houses a controller which controls actuating elements which may include a pump and a series of valves to control and direct the flow of liquid within the fluidic device. In some embodiments the reader assembly may comprises multiple pumps. The sample and reagents are preferably pulled through the fluidic channels by a vacuum force created by sequentially opening and closing at least one valve while activating a pump within the reader assembly. Methods of using a valve and pump to create a vacuum force are well known. While a negative pulling force may be used, a positive or pushing force may also be generated by at least one pump and valve according to the present invention. In other embodiments movement of fluid on the fluidic device may be by electro-osmotic, capillary, piezoelectric, or microactuator action.

Figure 5:
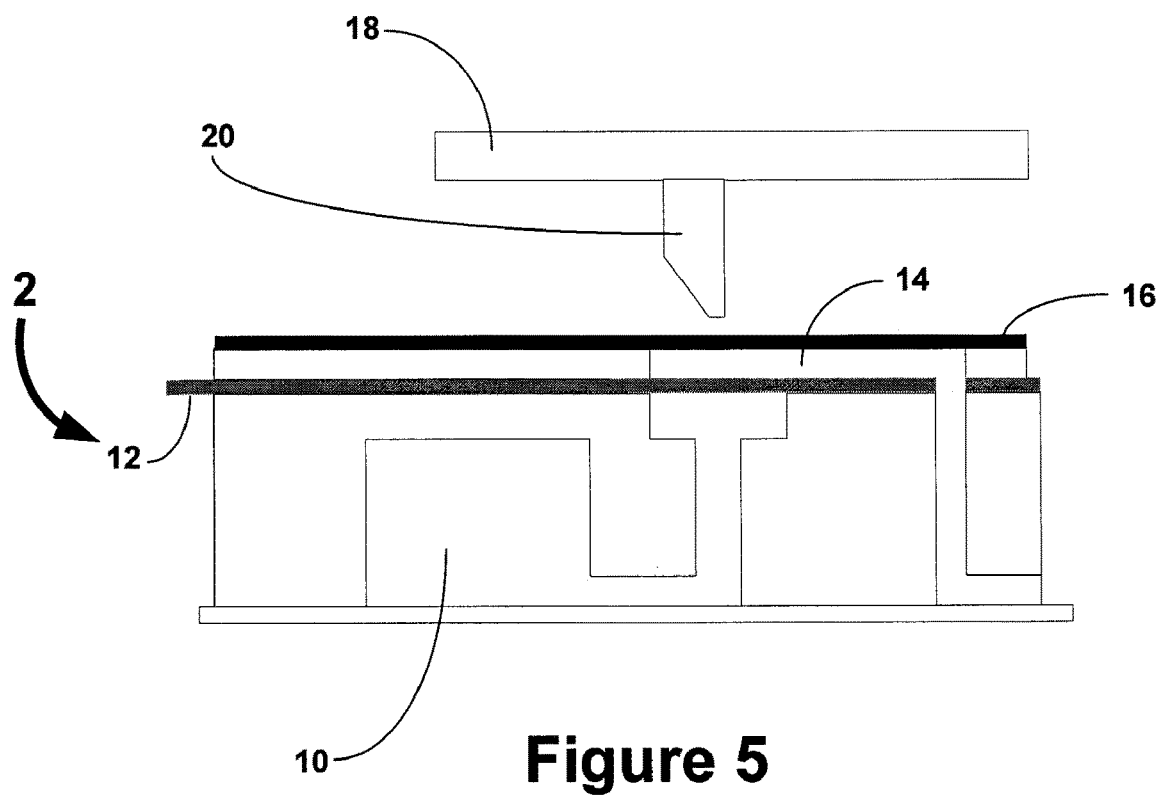
FIGS. 5 and 6 illustrate a side view of an exemplary fluidic device is combination with actuating elements of the reader assembly.
Figure 6:
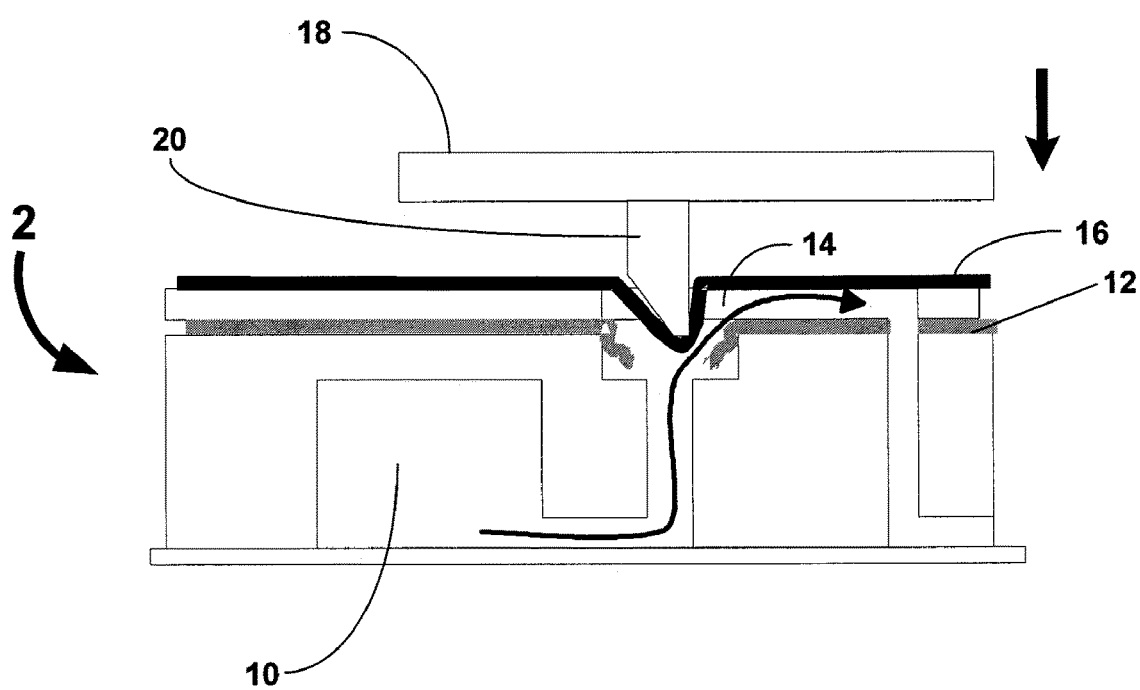

FIGS. 5 and 6 illustrate an exemplary sequence to initiate the flow of a reagent within the fluidic device. An actuation plate 18 in the reader assembly comprises a non-coring needle or pin 20 which when lowered flexes the top cover 16, as it is preferably made of strong, flexible elastomeric material. However, the easily rupturable foil 12 then ruptures due to the stress induced by the flexing of top cover 16. Valves located downstream to the reagent chamber 10 puncture different areas of foil in the fluidic device and can then work in tandem with a pump within the reader assembly to create a vacuum force to pull the reagent out of the reagent chamber 10 into a fluidic channel 14 and then direct the flow of the reagent to a reaction site. At least one valve is preferably fluidically connected to a pump housed within the reader assembly. One of the advantages of this embodiment is that no on-chip pump is required, which, at least, decreases the size and cost of the fluidic device, and allows the device to be disposable.

A reaction assembly preferably houses a detection assembly for detecting a signal produced by at least one assay on the fluidic device. FIG. 1 illustrates an exemplary position of a detection device below the fluidic device after it is inside the reader assembly. The detection assembly may be above the fluidic device or at a different orientation in relation to the fluidic device based on, for example, the type of assay being performed and the detection mechanism.

A communication assembly is preferably housed within the reader assembly and is capable of transmitting and receiving information wirelessly from an external device. Such wireless communication may be bluetooth or RTM technology. Various communication methods can be utilized, such as a dial-up wired connection with a modem, a direct link such as a T1, ISDN, or cable line. In preferred embodiments a wireless connection is established using exemplary wireless networks such as cellular, satellite, or pager networks, or a local data transport system such as Ethernet or token ring over a local area network. In some embodiments the information is encrypted before it is transmitted over a wireless network. In some embodiments the communication assembly may contain a wireless infrared communication component for sending and receiving information.

In preferred embodiments an external device communicates with the communication assembly within the reader assembly. An external device can wirelessly communicate with a reader assembly, but can also communicate with a third party, including without limitation a patient, medical personnel, clinicians, laboratory personnel, or others in the health care industry.

In some embodiments the external device can be a computer system, server, or other electronic device capable of storing information or processing information. In some embodiments the external device includes one or more computer systems, servers, or other electronic devices capable of storing information or processing information. In some embodiments an external device may include a database of patient information, for example but not limited to, medical records or patient history, clinical trial records, or preclinical trial records. In preferred embodiments, an external device stores protocols to be run on a fluidic device which can be transmitted to the communication assembly of a reader assembly when it has received an identifier indicating which fluidic device has been inserted in the reader assembly. In some embodiments a protocol can be dependent on a fluidic device identifier. In some embodiments the external device stores more than one protocol for each fluidic device. In other embodiments patient information on the external device includes more than one protocol. In preferred embodiments the external server stores mathematical algorithms to process a photon count sent from a communication assembly and in some embodiments to calculate the analyte concentration in a bodily fluid sample.

A server can include a database and system processes. A database can reside within the server, or it can reside on another server system that is accessible to the server. As the information in a database may contains sensitive information, a security system can be implemented that prevents unauthorized users from gaining access to the database.

One advantage of the present invention is that information can be transmitted from the external device back to not only the reader assembly, but to other parties or other external devices, for example without limitation, a PDA or cell phone. Such communication can be accomplished via a wireless network as disclosed herein. In some embodiments a calculated analyte concentration or other patient information can be sent to, for example but not limited to, medical personal or the patient.

In some embodiments a sample of bodily fluid can first be provided to the fluidic device by any of the methods described herein. The fluidic device can then be inserted into the reader assembly. An identification detector housed within the reader assembly can detect an identifier of the fluidic device and communicate the identifier to a communication assembly, which is preferably housed within the reader assembly. The communication assembly then transmits the identifier to an external device which transmits a protocol to run on the fluidic device based on the identifier to the communication assembly. A controller preferably housed within the reader assembly controls actuating elements including at least one pump and one valve which interact with the fluidic device to control and direct fluid movement within the device. In some embodiments the first step of the assay is a wash cycle where all the surfaces within the fluidic device are wetted using a wash buffer. The fluidic device is then calibrated using a calibration assembly by running the same reagents as will be used in the assay through the calibration reaction sites, and then a luminescence signal from the reactions sites is detected by the detection means, and the signal is used in calibrating the fluidic device. The sample containing the analyte is introduced into the fluidic channel. The sample may be diluted and further separated into plasma or other desired component at a filter. The separated sample now flows through the reaction sites and any present analytes bind to probes bound thereon. The plasma of sample fluid is then flushed out of the reaction wells into a waste chamber. Depending on the assay being run, appropriate reagents are directed through the reaction sites to carry out the assay. All the wash buffers and other reagents used in the various steps, including the calibration step, are collected in wash tanks. The signal produced in the reaction sites is then detected by any of the methods described herein.

The term "analyte" according to the present invention includes without limitation drugs, pharmaceutical agents, drug metabolites, biomarkers such as expressed proteins and cell markers, antibodies, serum proteins, cholesterol, polysaccharides, nucleic acids, biological analytes, biomarker, gene, protein, or hormone, or any combination thereof.

Communication between a reader assembly and an external storage device allows for a reader assembly of the present invention to download a fluidic device-specific protocol to run on the fluidic device based on the identity of the fluidic device. This allows a reader assembly to be used interchangeably with any appropriate fluidic device described herein. In addition, the external device can store a plurality of protocols associated with a given fluidic device, and depending on, for example, a subject's treatment regime or plan, different protocols can be communicated from the external device to the reader assembly to be run on the fluidic device to detect a variety of analytes. The external device can also store a plurality of protocols associated not only with a fluidic device, but also with a particular subject or subjects, such that a protocol can be associated with a subject as well as with a fluidic device.

In some embodiments a method of improving the accuracy of an assay performed on a fluidic device used to detect an analyte in a bodily fluid comprises providing a system for detecting the presence of an analyte in a bodily fluid from a subject comprising a fluidic device for providing said bodily fluid and a reader assembly for detecting the presence of said analyte, and providing a sensor to detect a change in said system which may alter the accuracy of said detecting said presence of said analyte.

In some embodiments a sensor may be present either in the fluidic device, the reader assembly, both, or in some cases it may be advantageous to include a sensor in the packaging in which the fluidic device and/or reader assembly are packaged. The sensor can, for example without limitation, detect temperate or pressure changes that may provide for an inaccurate analyte concentration calculation. For example, if the temperature of reagents stored in said fluidic device falls outside an acceptable temperature range, this may indicate that the detection will not be accurate using the then existing calibration and processing algorithms, for example. Likewise, for example, the pressure in the pump in the reader assembly may fall outside an acceptable range. In some embodiments a moisture sensor is provided to detect the presence of moisture in the cartridge before the assay begins. In some embodiments there may be thiocyanate in one layer of the fluidic device and iron salt in another layer, wherein a dye is formed when these are mixed, whereby the dye is a visual indication of the presence of moisture.

In some disposable systems, particularly in those where sample acquisition is performed by the patient or end user, measurement errors are not uncommon. Significant errors due to, for example, patient handling of the sample, could be due to the sample collection method. A patient may not collect the correct volume of the sample, the collection may not be performed at the appropriate time, or the sample may not be handled in an appropriate manner, thus compromising the sample integrity. It may be advantageous when using a disposable system in which the patient controls the initial sample collection and handling to utilize methods for minimizing the consequences of such errors by, for example, either alerting the patient to repeat the test or use calibration steps to compensate for such errors.

Immunoassays have a characteristic response similar in form to the well-known Scatchard binding isotherm (Bound/Maximum Bound (B/B0)=Ligand Concentration/(K+Ligand Concentration) where B is the amount of the labeled analyte bound to a solid phase when analyte is present, B0 is the amount bound when no analyte is present and K is the dissociation constant. The mathematical form of such assay responses is hyperbolic.

Figure 21:
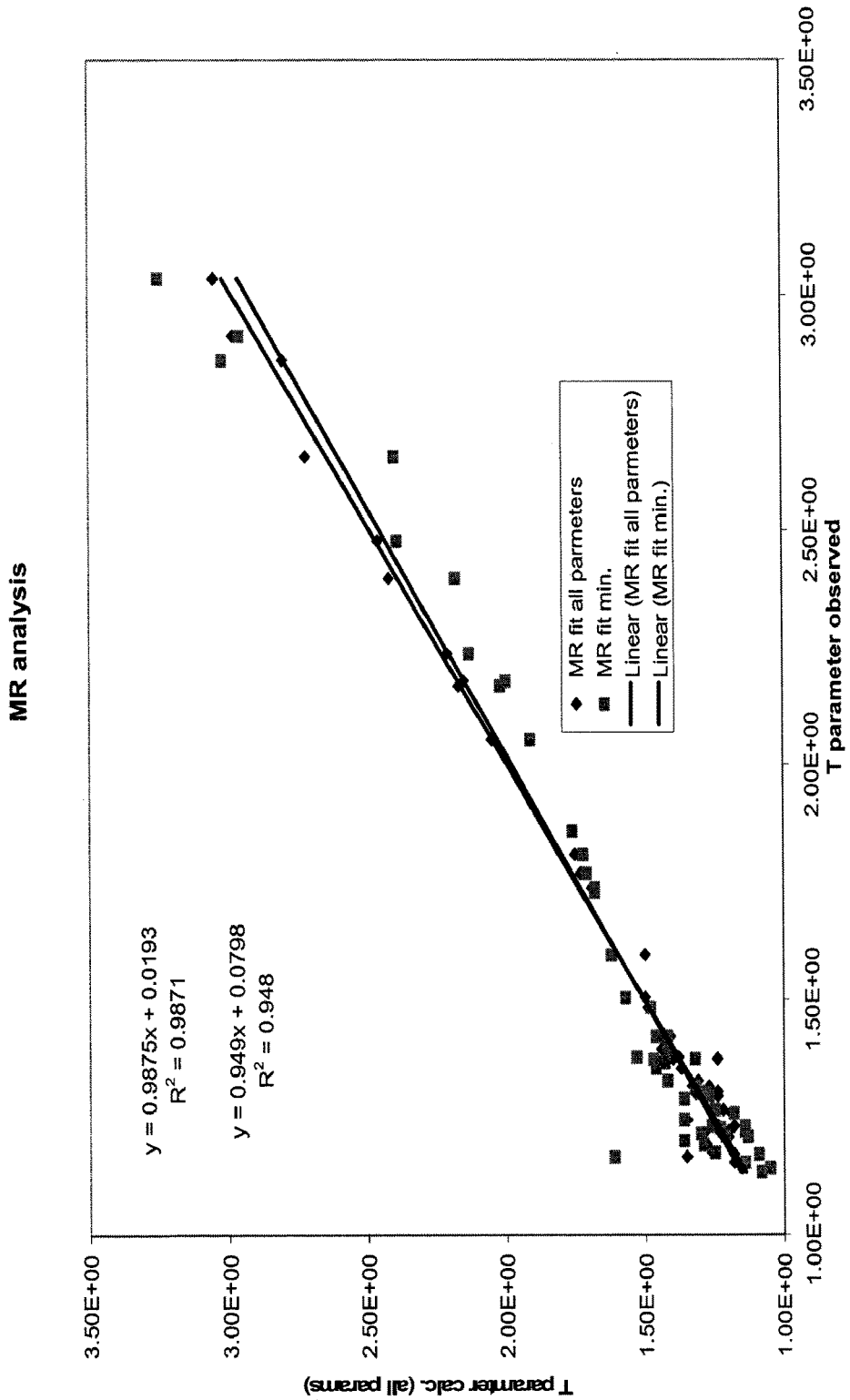
FIG. 21 shows multiple regression analysis of the computed therapeutic index.

Results of immunoassays of the types described above are typically analyzed using the known (ln-logit) or (log-logit) functions, in which the assay label (for example in a two-step process, alkaline phosphatase-labeled analyte) bound to a solid phase when analyte is present in the assay ("B") is compared with the amount bound when no analyte is present ("B0") to provide the ratio B/B0. Then, the "logit" function (logit=Log [(B/B0)/(1−B/B0)]) is plotted against Log (Analyte Concentration) resulting in a straight line. (Natural logarithms can also be used instead of logarithms to base 10). The slope and intercept of this plot can be used to derive simple equations that permit the calculation of (a) assay signal as a function of analyte concentration, or (b) analyte concentration as a function of assay signal. An example of such analysis is shown in FIG. 21 using Thromboxane as the analyte of interest. The best fit to the data is given by Equation 1: Signal=(A−D)/(1+(Analyte conc./C)^B)+D [Equation 1], where A is the signal at zero analyte concentration, D is the signal at infinite analyte concentration, C is the analyte concentration reached at a signal level half way between A and D, and B is a shape parameter. The relationship between analyte concentration and signal is given by: Analyte concentration=C*((((A−D)/(Signal−D)−1)^(1/B)) [Equation 2], where A, B, C and D are identical to the parameters used in Equation 1.

It is possible to compute errors that occur from miscalibration using the equations described herein above. (The Analyte Concentration function from Equation 2 is differentiated with respect to each potential variable A, B, C, D and Signal). Estimates of the difference between the ideal value of the variable and the actual value in the system are used as Δ values in the calculation (Δ(concentration)=(d(Concentration)/d(Param.))*Δ Param). Errors in calibration are reflected in erroneous values of A, B, C and D. Each of these parameters is influenced by a different factor. For example, temperature effects on calibration of immunoassays will have the strongest impact on the A, C and D parameters of the in-logit calibration, while likely having a minimal impact on the shape parameter B. The detected signal, which in turn can be used to determine the analyte concentration, is biased by one or more of the following reader assembly and fluidic device characteristics: optics used in the instrument for signal measurement; temperature control; most chemical processes are highly temperature sensitive, including enzyme reactions, and equilibrium between antigens and antibodies; timing of assay steps; calibration relative to an "ideal" instrument; the inability of the patient to manually recalibrate the fluidic device when used; dimensions of the fluidic device; volume of the assay assembly and its shape; fluid movement within the device; timing and uniformity of fluid movement; efficiency in mixing (most assay methods used in disposables and employ microfluidics would involve some mixing). The following reagent variations can also contribute to a biased detected signal: reagent quantity; reagent dissolution (if it is in dry form); changes in activity of reagents following manufacture (instability) (This is particularly important for "distributed systems" where the disposable useful life is typically determined by reagents which can, for example, lose 20% of their activity. If they can be used without significantly compromising assay performance, the shelf-life of many expensive disposables could be extended several fold and severe constraints on disposable storage (refrigeration and the like) can be relaxed). In addition, when calibration is performed at the factory, small errors in the estimation of the calibration parameters can result in error in the calculated analyte concentration.

Figure 7:
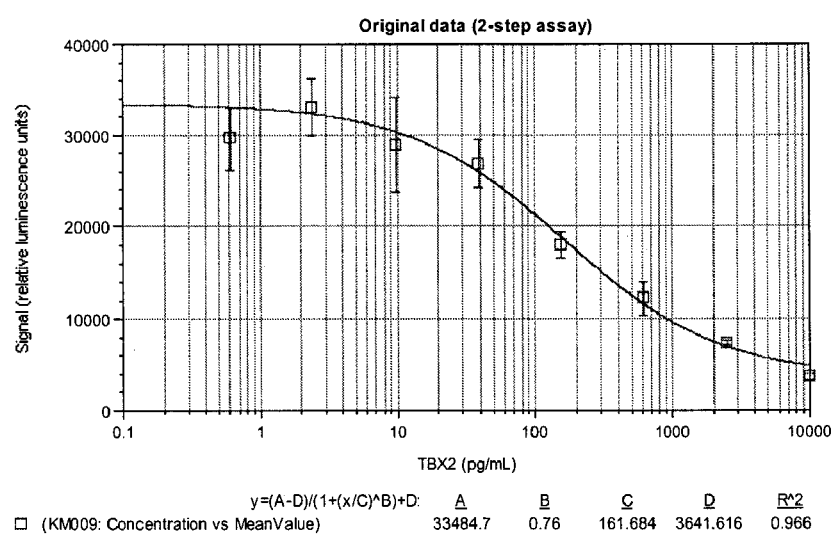
FIG. 7 shows a typical assay dose-response data for a two-step assay for TxB2.
Figure 8:
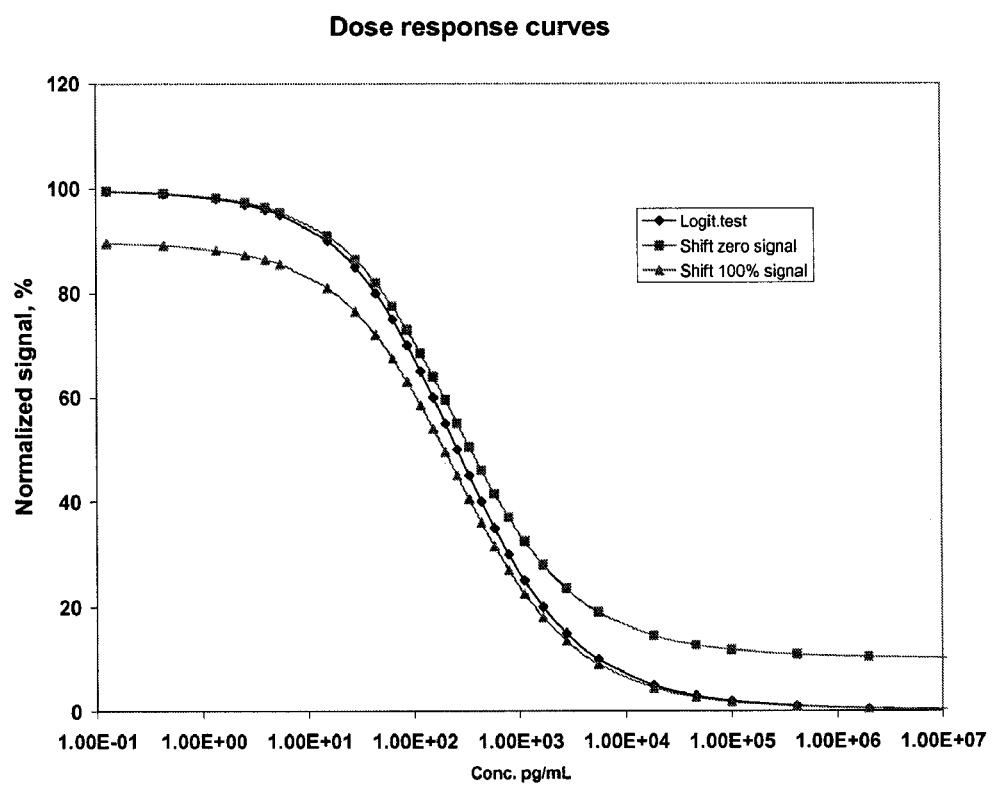
FIG. 8 shows dose responses computed with and without errors in calibration parameters.
Figure 9:
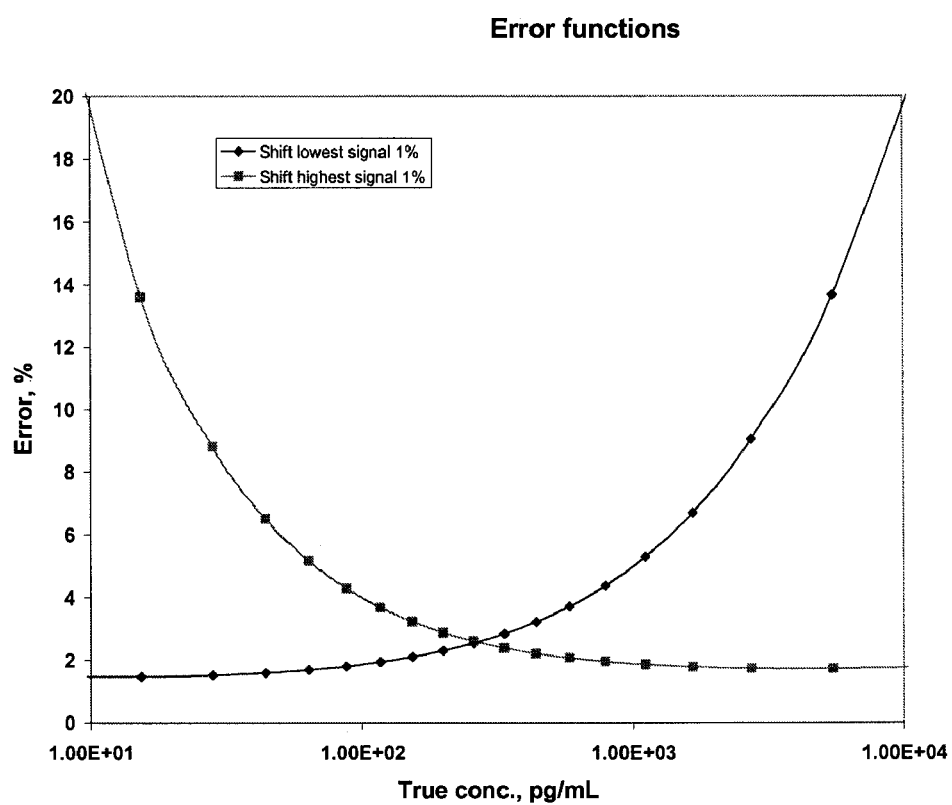
FIG. 9 shows computed concentration errors produced by 1% mis-estimation of A and D calibration values.

The magnitudes of these calibration errors and consequently errors introduced in estimating analyte concentrations can be quite significant. FIG. 7 shows the dose-response data for a two-step assay for Thromboxane. The top curve (Logit.test) in FIG. 8 shows a typical (ln-logit) assay response. When we adjust the level of the highest signal (A) and the lowest signal (D), shown as "Shift zero signal" and "Shift 100% signal", respectively, the curves shift as seen in FIG. 8. The corresponding computed values of error in the concentration that would be calculated from Equation 2 were large (>20% across the entire range of the assay) as shown in FIG. 9. In FIG. 8, the signal is normalized by subtracting the D value from the signal and dividing the difference by (A–D):(Signal–D)/(A–D). This yields what is usually described as $B/B_0$ (the ratio of bound label at a given analyte concentration to that at zero analyte level). The ln-logit function was modified by adding 10% of (A–D) to D or subtracting 10% of (A–D) from A before recalculating the normalized signals (corresponding to two types of significant calibration error (shifting the value of A or D respectively). At signal levels intermediate between A and D the change made was adjusted by 10%*(Original signal–D)/(A–D). FIG. 9 shows that when modifications of only 1%*(A–D) were made, and concentration of the analyte was computed, errors in concentration were still significant at certain parts of the analyte concentration range.

Conventionally, a calibration exercise is performed in parallel with assaying the sample. This is, however, impractical in a self-contained, disposable assay system intended to be compact and inexpensive. To address any calibration challenges that may occur while assaying analytes using a fluidic device of the present invention, in some embodiments parameters A, or in preferred embodiments A and D, of Equation 1 described herein above, are measured within the fluidic device rather than using manufacturer's values or an external device. The value(s) is compared with the parameter values estimated when the fluidic device was calibrated by the manufacturer. Signal results are then adjusted using the following equation: $Signal_{adjusted} = Signal * (A_{factory\ calibration} / A_{measured\ within\ the\ assay})$ and the original calibration equation (Equation 1) is then used to calculate the analyte concentration. Alternatively, A and D values measured at the time of assay are substituted for the A and D values obtained during factory calibration. Typically the (A/D) calibration measurement would be made in a buffer sample, preferably for each analyte (in a multiple analyte assay device), or one analyte only, if each assay responds similarly to the various factors that alter the calibration parameters.

In some embodiments of this invention, the calibration parameters of Equation 1 are corrected using differential calibration. The following example using Thromboxane B2 as the analyte illustrates this approach. Thromboxane B2 (TxB2) (1.25 mg) was dissolved in a mixture of dimethyl-sulfoxide (342 µl) and water (342 µl). To this, 5 µl of a solution of 1-(3-(dimethylamino)propyl)-3-ethyl-carbodiimide hydrochloride in water (0.1 g/ml) and 10 µl of a solution of n-hydroxy-succinimide in water (0.1 g/ml) were added. After 1 hour at room temperature the resulting NHS-ester of TxB2 was used in the preparation of TxB2 labeled with alkaline phosphatase (described below) without further purification. Alkaline phosphatase (bovine intestine, Sigma-Aldrich) was dissolved in phosphate-buffered saline at 1 mg/ml. To 1 ml of this solution 120 IA of the NHS-ester of TxB2 was added and the mixture allowed to react for 1 hour at room temperature. The enzyme-TxB2 conjugate was then purified overnight by dialysis against tris-buffered saline containing $MgCl_2$.

Described is an example of a two-step enzyme immunoassay where TxB2 is the analyte. Samples and mouse monoclonal anti-TxB2 (15 µl of Cayman Chemical Kit Catalog number 10005065, appropriately diluted into Assay Designs buffer) were added to 384-well plates to which anti-Mouse IgG had been immobilized ((Becton Dickenson 356177)). The sample was 30 µl of plasma diluted 1:4 with assay buffer (Assay Designs Correlate-CLIA™ kit 910-002) and supplemented with known concentrations of TxB2. Other types of sample (for example TxB2 dissolved in assay buffer) can be substituted.

Plates were covered to prevent evaporation and incubated at room temperature with gentle mixing (100 rpm) on an orbital shaker for 12 hours. The contents of the wells were then removed by aspiration. Thromboxane-labeled with alkaline phosphatase (25 µl diluted 1:1500 with assay buffer) was added and incubated at room temperature for 2 minutes. The contents of the wells were removed by aspiration and wells washed thrice with 100 µl wash buffer (from the Assay Designs Kit 910-002).

Enzyme bound to the wells was then measured by addition of 40 µl Lumiphos™ 530 substrate solution which contains (4-methoxy-4-(3-phosphate-phenyl-spiro-[1,2-dioxetane-3,2'-adamantane])). Incubation was allowed to proceed for 1 hour with orbital mixing and the luminescent product measured in a Molecular Devices MD5 Spectrometer (0.5 second integration time).

FIG. 7 shows the typical assay dose-response data for a two-step assay for TxB2. Using Equation 1, the parameters A, B, C and D are fitted to the curve shown in FIG. 7. As described herein, even small changes in values of the parameters A and D can have a significant impact on the measured concentration. Thus, any errors in computing A and D are magnified in the estimated analyte (TxB2) concentration. This concept is illustrated in FIGS. 8 and 9, where even a 1% change in (A–D) resulted in significant errors in estimating TxB2 concentrations in the samples. In FIG. 8, the signal is normalized by subtracting the D value and dividing the difference by (A–D) viz: (Signal–D)/(A–D). This calculates what is commonly described as B/B0 (the ratio of bound label at a given analyte concentration to that at zero analyte level). The (ln-logit) function was modified by adding 10% of (A–D) to D or subtracting 10% of (A–D) from A before recalculating the normalized signals (corresponding to two types of significant calibration error (shifting the value of A or D respectively). At signal levels intermediate between A and D, the change made was adjusted by 10%*(Original signal–D)/(A–D). FIG. 9 shows the computed errors in estimating the analyte concentrations for a 1% error in estimating A and D. As can be seen for the low analyte concentrations, the errors are pronounced even for small errors in the calibration parameters A and D.

Figure 10:
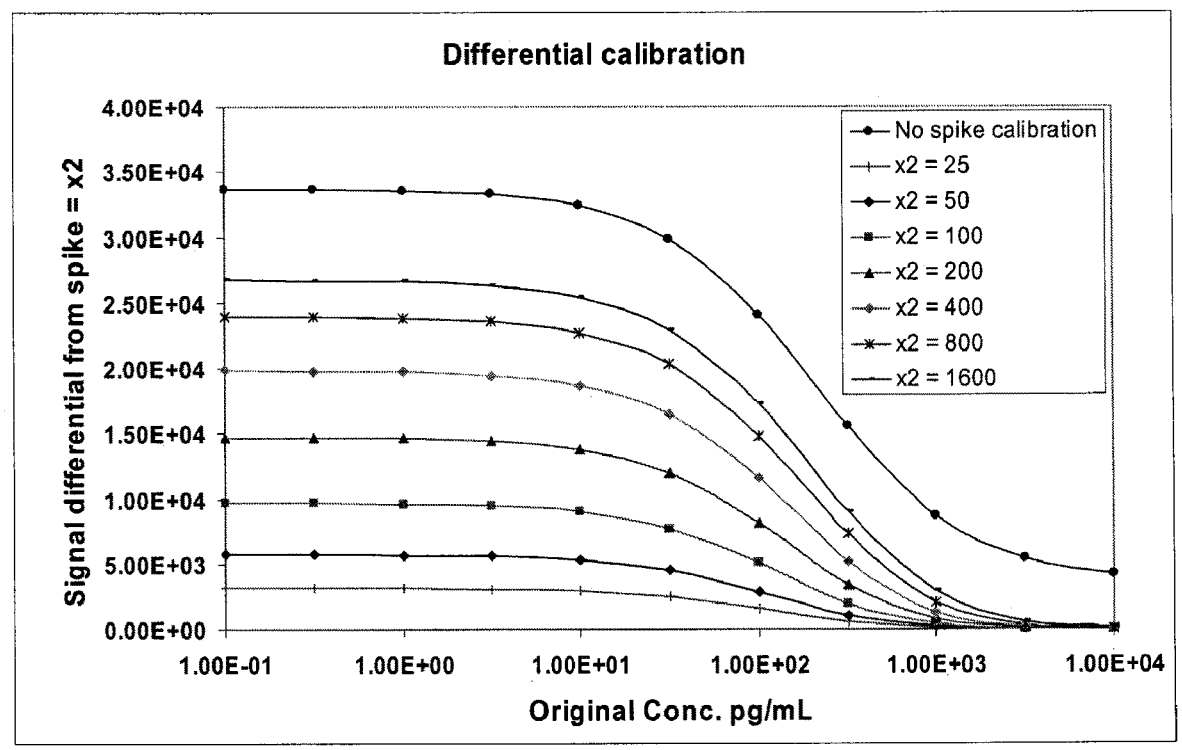
FIG. 10 illustrates calibration using a "differential" approach.

FIGS. 10-13 illustrate an embodiment of this invention where the sample containing an unknown analyte concentration is spiked with a known concentration of the analyte to minimize calibration errors. Spiking can be achieved by a variety of methods, for example, by incorporating analyte in known quantities to the assay well during manufacture of the fluidic device. Separate spike wells could also be accommodated in the fluidic device described herein. FIG. 10 shows calibration using differences between signal response between unspiked and spiked samples. The amount of the spiked analyte is indicated by x2 and the original (endogenous concentration in the sample) is denoted as original concentration or x1 (pg/ml). The difference in signal between unspiked and spiked sample is plotted against the signal for the original concentration for various amounts of known amount of analyte (spike) introduced into the sample. The (ln-logit) parameters (for the top curve in FIG. 10) are shown in Table 1.

TABLE 1

Original Calibration Parameters for Data Shown in FIG. 10

| A | 3.37E+04 |
|---|---|
| B | 1.01E+00 |
| C | 2.10E+02 |
| D | 3.56E+03 |

The data shown in the top curve in FIG. 10 were used in a recalibration exercise by calibrating against the difference in signal for each original concentration level and each level spiked with 200 pg/ml analyte. Equation 3 shown below was empirically derived and is useful in calculating the original endogenous concentration of analyte. The best-fit parameter values in Table 2 were computed by minimization of the sum of the square of the differences between target and calculated analyte values. Concentration=$C*((A-D)/((Signal-D)^{(1/B)})+E$ [Equation 3].

TABLE 2

Calculated Parameter Values for 1-point Spike Calibration

| A | 1.20E+02 |
|---|---|
| B | 1.996189 |
| C | 292.7824 |
| D | −0.14393 |
| E | −287.931 |

Figure 11:
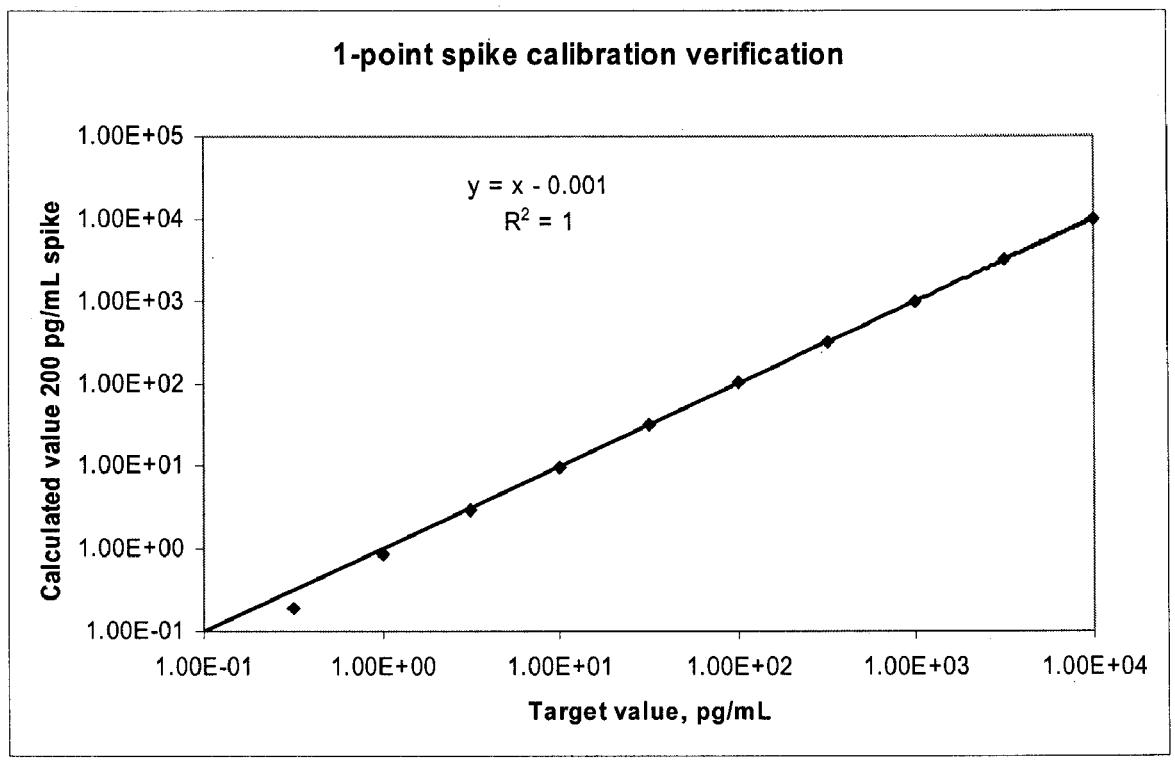
FIG. 11 shows the verification of calibration using the "1-point spike" method (log scale).
Figure 12:
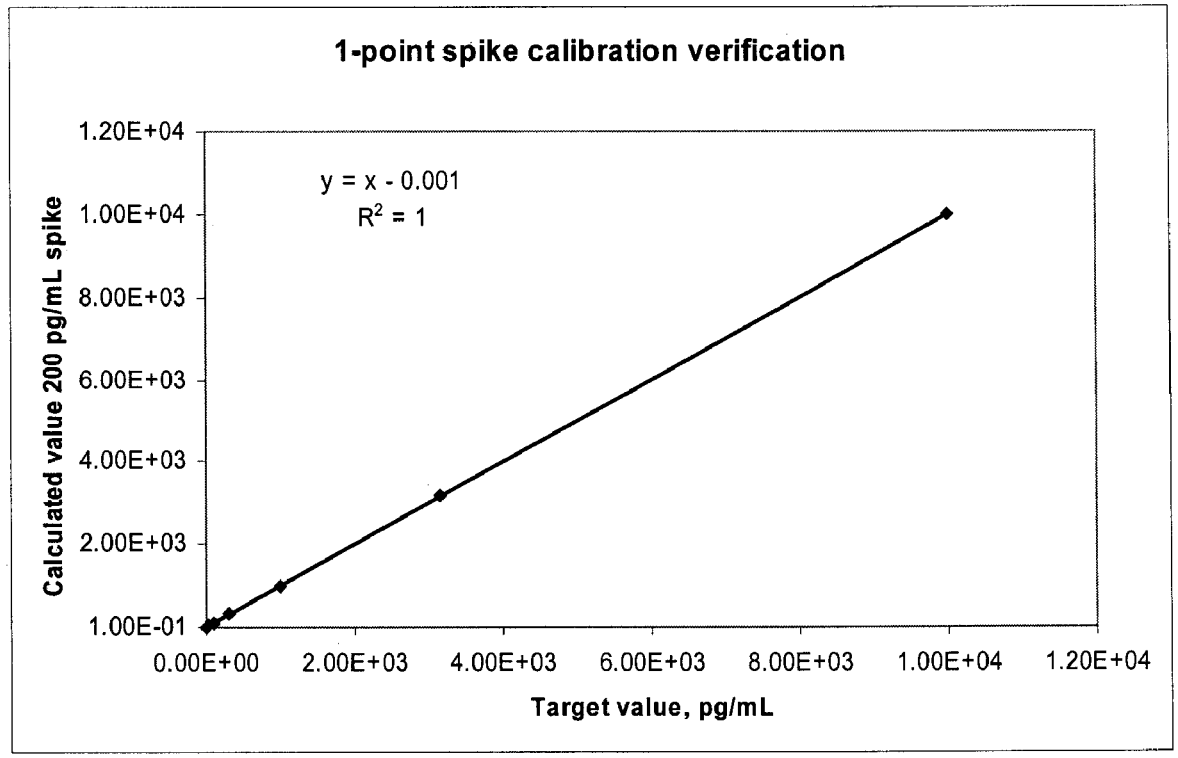
FIG. 12 shows the verification of calibration using the "1-point spike" method (linear scale).

This calibration was verified as shown in FIG. 11 (log scale) and FIG. 12 (linear scale). Note the regression equation was calculated for data in linear form. The formula resulted in near perfect results.

Figure 13:
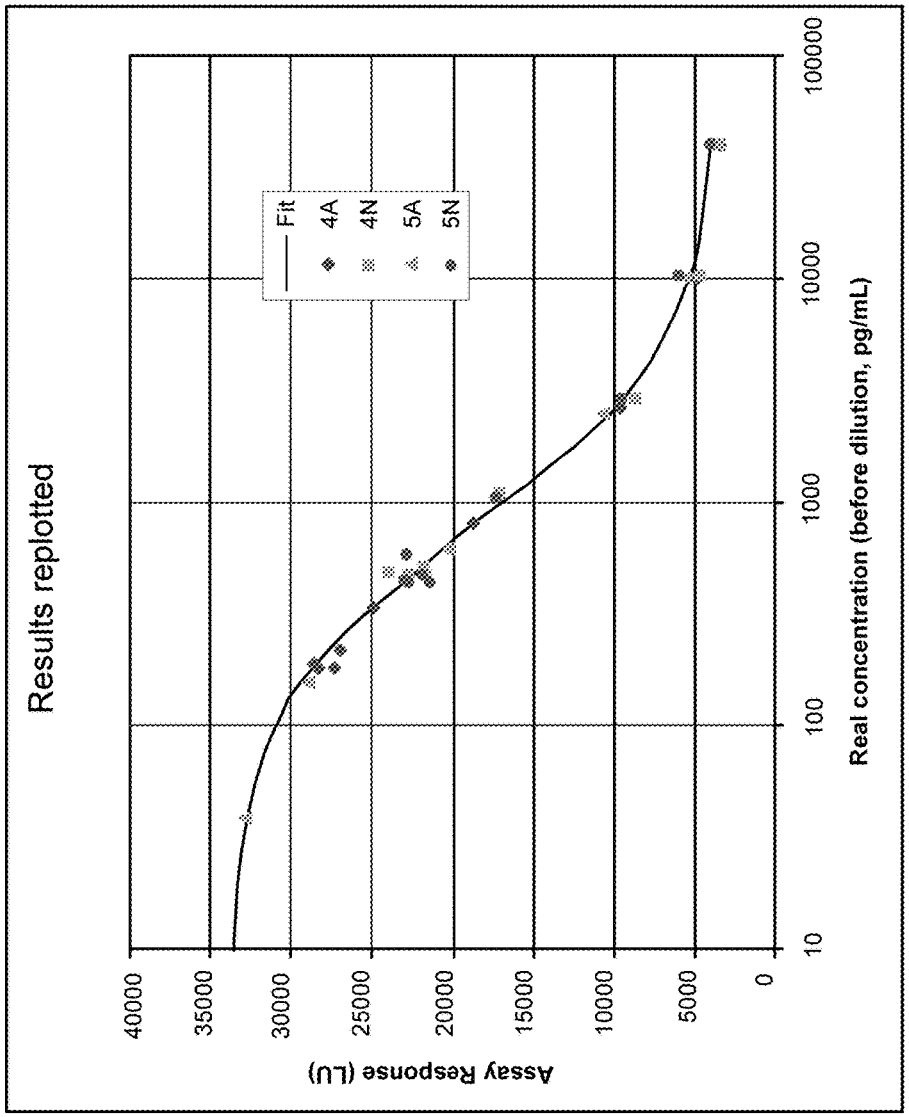
FIG. 13 shows dose-response of assays calibrated against a plasma sample with a very low TxB2 concentration.

The results of one embodiment of this invention are shown in FIG. 13, where the extent of the recovery of the spike signal is used to correct for the concentration of the value of the unspiked sample. This method has the advantage that changes in the parameter C in the (ln-logit) equation due to, for example, reagent instability, are accounted for. The method involves the following steps: calculate x1 (endogenous conc.), and x2 (spike conc.) using original calibration; calculate recovery of spike as % (x2−x1)/spike [Equation 4]; correct x1 by recovery factor: (x1*100/Spike recovery) [Equation 5].

Figure 14:
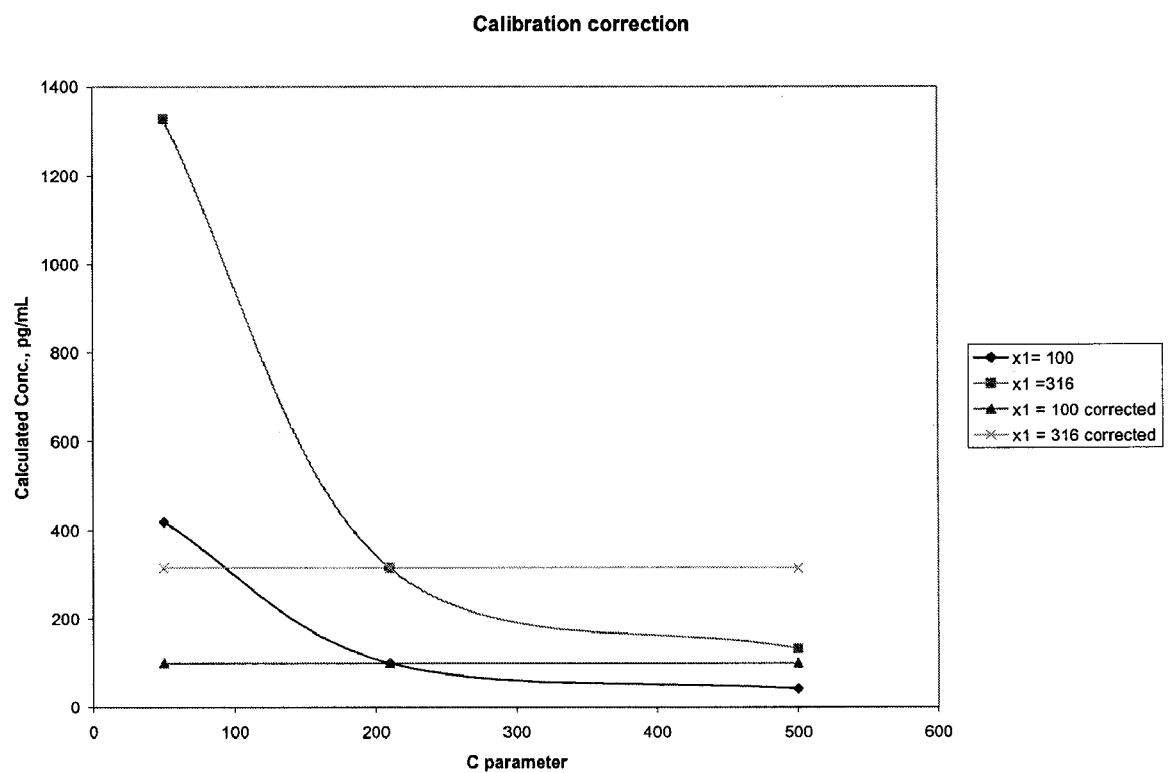
FIG. 14 shows use of spike recovery to eliminate calibration errors of the "C" parameter.

This was tested with the calibration curve shown in FIG. 10 and the original calibration parameters of Table 1. As shown in Table 3, it was possible to use spike concentration values from 100-500 pg/ml and C values that varied from 500 to 50 such that the actual signals corresponding to the modified C values were changed very significantly from what had been the case with the original C value and the spike recovery (calculated with the original C value ranged from 42-420% respectively, yet the recovery of the unspiked sample (once corrected for the recovery of the spike) was 100% over the entire calibration range. This effect is graphically illustrated in FIG. 14, where the C parameter is varied between 50 and 500 (a ten fold range), but the corrected values for the analyte concentration (x1) accurately reflects the expected analyte concentration.

TABLE 3

Effects of changes in the C parameter on spike and original analyte recovery at two original concentration levels

| C | x1 Pg/ml | S (x1) | x2 pg/ml | S (x1 + x2) | x2 recovery % | x1 recovery % |
|---|---|---|---|---|---|---|
| 500 | 100 | 2.88E+04 | 500 | 1.73E+06 | 42 | 100 |
| 210 | 100 | 2.40E+04 | 500 | 1.13E+04 | 100 | 100 |
| 50 | 100 | 1.36E+04 | 500 | 5.83E+03 | 420 | 100 |
| 500 | 316 | 2.21E+04 | 500 | 1.50E+04 | 42 | 100 |
| 210 | 316 | 1.56E+04 | 500 | 9.66E+03 | 100 | 100 |
| 50 | 316 | 7.61E+03 | 500 | 5.25E+03 | 420 | 100 |
| 500 | 100 | 2.88E+04 | 200 | 2.25E+04 | 42 | 100 |
| 210 | 100 | 2.40E+04 | 200 | 1.60E+04 | 100 | 100 |
| 50 | 100 | 1.36E+04 | 200 | 7.80E+03 | 420 | 100 |
| 500 | 316 | 2.21E+04 | 200 | 1.84E+04 | 42 | 100 |
| 210 | 316 | 1.56E+04 | 200 | 1.22E+04 | 100 | 100 |
| 50 | 316 | 7.61E+03 | 200 | 6.16E+03 | 420 | 100 |

In Table 3, x1 is the endogenous concentration and x2 is the spike concentration; S is the signal level corresponding to the designated analyte concentration; x2 recovery is the apparent recovery of x2 and x1 recovery is calculated (using Equation 5) after compensating for x2 recovery (using Equation 4).

The spike level must be carefully chosen. The optimal level will be a compromise between the operating range of the assay and the likely range of concentrations of samples. If it is too low, the change in signal caused by the spike will be too small to be reliably measured. If it is too high, the assay response will be too shallow to reliably measure the spike. The ideal spike level would change the measured signal by much more than the standard deviation in the signal. In the above example, the assay range had been adjusted to make measurements for sample with concentrations in the range of about 0 to about 500 pg/ml and spikes of about 200 to about 1000 pg/ml would likely be useful.

In some embodiments the following various guidelines for choosing spike levels can be followed: spikes should change the observed signal across the desired range by at least 10%; spikes should be in the same range as the anticipated mid range of sample concentrations; spikes should be less than about three times the original C value. Note that the useful part of the dose-response is from about 0.2*C to about 5*C.

The following example illustrates the estimation of endogenous TxB2 concentrations using spike recovery. Two citrated human plasma samples were analyzed by the two-step assay. Aliquots of the samples were also supplemented (spiked) with known concentrations of TxB2 prior to assay. Some samples were also supplemented with indomethacin (0.1 mM) and/or EDTA (5 mM). Samples were stored either flash-frozen then thawed or refrigerated unfrozen prior to assay. These procedures generated a set of samples with various original endogenous concentrations (storage and freezing and thawing tends to cause platelet activation and production of TxB2; indomethacin inhibits TxB2 production).

The results of the above experiment are shown in FIG. 13. Sample 5A was known to have a very low TxB2 concentration (estimated to be <10 pg/ml). When the dose-response of the assay in sample 5 was used to calibrate the assay, the concentration was assumed to be zero. Dose responses for the other samples 4A, 4N, 5N were then plotted and it was observed that their response corresponded to higher concentrations of TxB2 and could be fitted to the 5N response by moving each to the left (in the direction of lower concentration) by an amount corresponding to removing a certain fixed TxB2 concentration from each the known spike levels. All the samples had responses that were almost identical in shape to that of sample 5N. When the curves fitted as closely as possibly to the A5 curve, the concentration of TxB2 notionally removed corresponds to the estimate of the TxB2 concentration in the sample.

Figure 15:
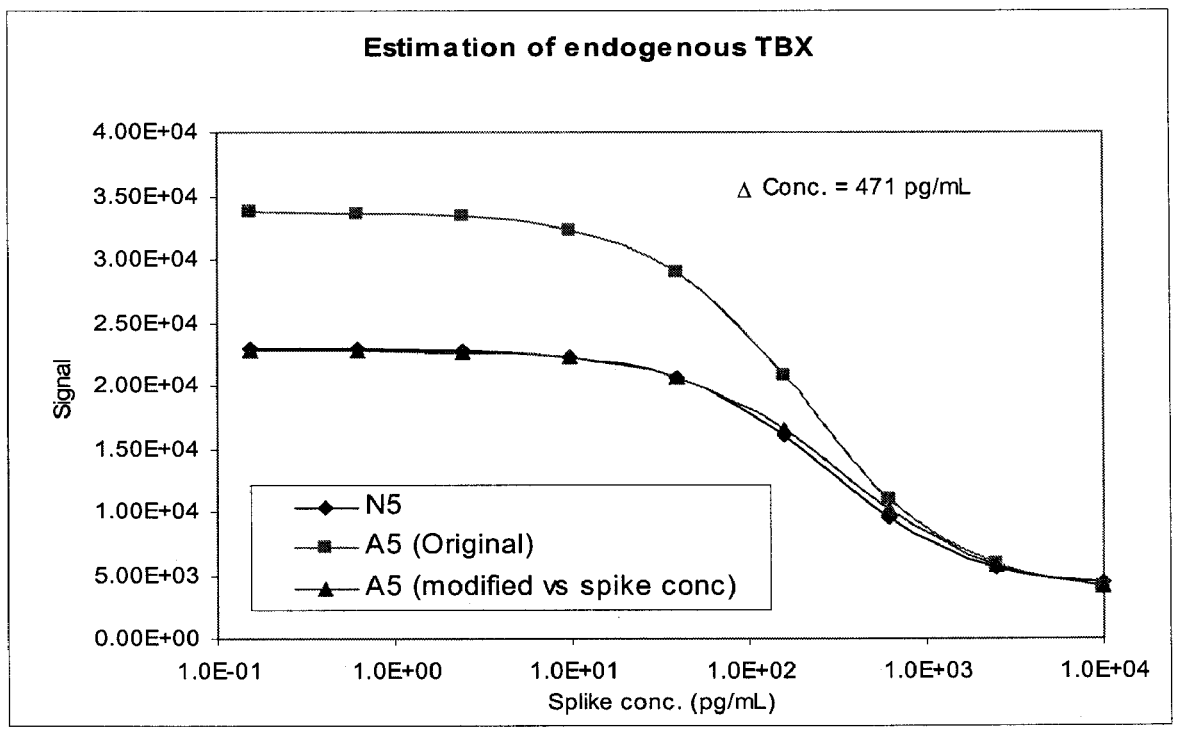
FIG. 15 illustrates calculating differences in concentration between two samples.

The original data of FIG. 13 were represented in FIG. 15 by the best fit (ln-logit) approximation. The Solver function in Microsoft Excel was used to compute a value of TxB2 that caused the A5 response to approximate that of the sample N5. As can be seen, this generated a good fit and the computed value (471 pg/ml) is an estimate of the concentration difference between TxB2 levels in the two samples.

Figure 16:
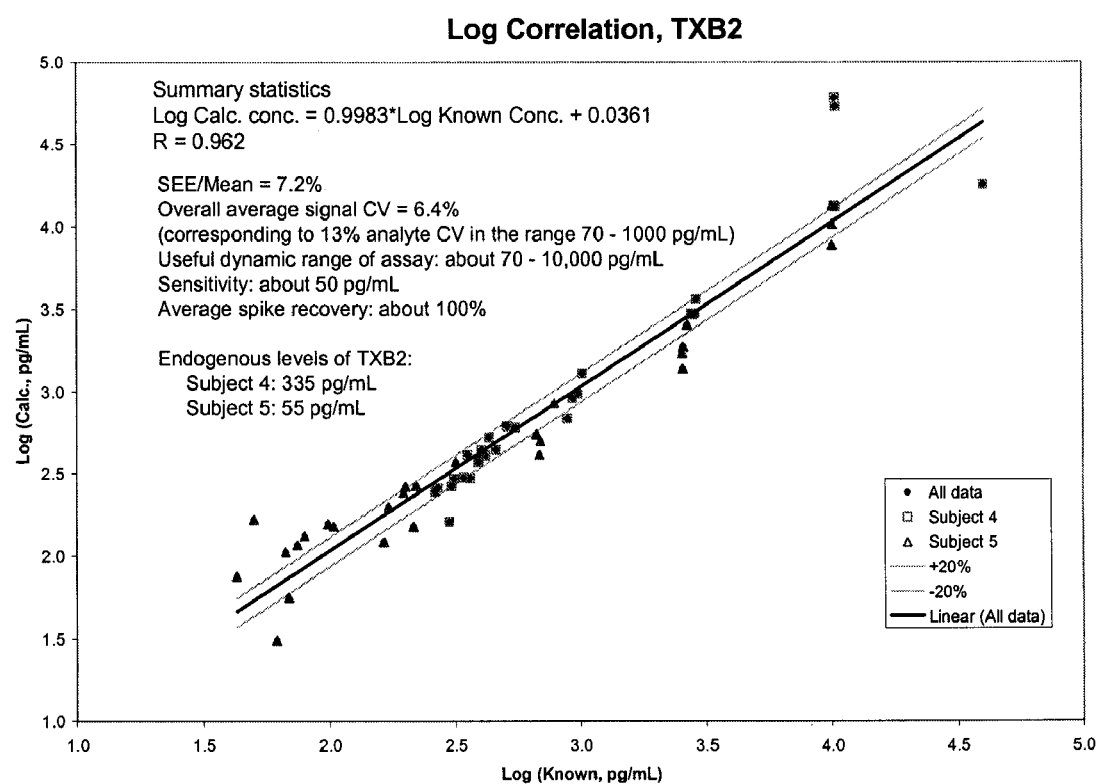
FIG. 16 illustrates an assay of plasma samples.

In another embodiment of our invention a single point can could be used (all the points fit closely to the calibration curve, so any single point could have been used) rather than a multi point spike that was illustrated in the earlier FIGS. 10-13. The following experiment illustrates this concept. Two plasma samples were spiked to many levels of TxB2 and assayed by the two-step method. Assays were calibrated using buffer calibrators rather than plasma-based materials. Results are presented in FIG. 16. Plasma was analyzed as described earlier. Data in FIG. 16 are plotted on a log scale. The concentration of unspiked samples was calculated from the calibration and the concentration of spiked samples taken as "endogenous+spike." Results are plotted only for the spiked samples. As can be seen, there was desirable correlation between the calculated and known values over the range of about 50 to about 10,000 pg/ml. When recovery was estimated for spikes in the range about 40 to about 2,500 pg/ml, the correlation was 99.7%.

Spike recovery method for correcting the calibration parameters are useful for compensating temperature effects on immunoassays in self-contained disposable analytical systems, also some times referred to as handheld analytical systems or assay systems. As is well known, instabilities in temperature during an assay introduce significant errors in the estimated analyte concentration. Temperature effects on calibration of immunoassays have the strongest impact on the A, C and D parameters of the (ln-logit) calibration. It is likely that the B (shape) parameter is minimally affected by temperature changes. As shown above, the spike recovery method can correct for errors introduced in the C parameter and hence could be an excellent approach for correcting temperature induced errors in computing the calibration parameters of the (ln-logit) equation. Similarly, normalizing signal levels to the zero analyte calibrator level, as described earlier, can compensate for errors in the A and D parameters, which are again negatively influenced by temperature changes.

Internal calibration and/or spike recovery means of calibration have significant advantages over conventional factory-calibration methods. One obvious advantage is that two quantities of assay-related information are used to compute the assay result rather than one, which improves the reliability of the assay. A second advantage is that this approach compensates, to a large extent, reagent instability. Another advantage is that several instrument, assay environment, and procedural variables are factored into the assay results.

Figure 17:
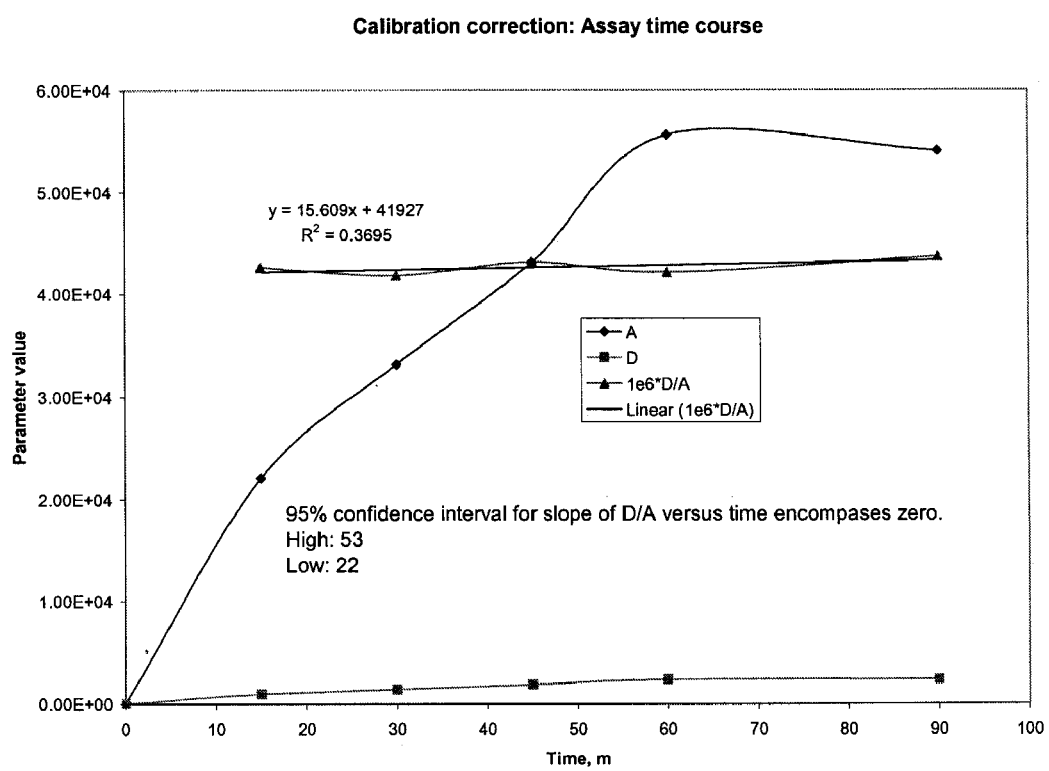
FIG. 17 shows the time course of assay signal generation.

Other uncontrolled changes in system response, besides temperate change, can also negatively impact the computed A and D parameters. For example, FIG. 17 shows the time course of the signal generation during an assay. To correct for these errors, one embodiment of the claimed invention is to compare assay signals B in a fluidic device with the B0 signal so to eliminate errors due to variation of the absolute value of assay signals due to uncontrolled changes in system response. This concept was verified by the following experiment.

A competitive immunoassay for TxB2 was set up using the protocol described in Assay Designs Product Literature for their corresponding Correlate-CLEIA kit (catalog 910-002). An alkaline phosphatase conjugate was prepared as described earlier and was diluted 1:112,000 and substituted for the kit conjugate. A and D parameters are the calibration parameters used in the (log-logit) fit to the assay response. Best fit values were obtained at each time point. Note that at zero time the A and D parameters are not measured, but all signal values would be (are known to be) zero. The ratio D/A was multiplied by 1e6 so as to be presentable on the same scale. The A and D values when plotted against time vary significantly, particularly the A value (zero analyte). As seen from the straight line with practically zero slope, the scaled D/A remains constant over the time span.

Figure 18:
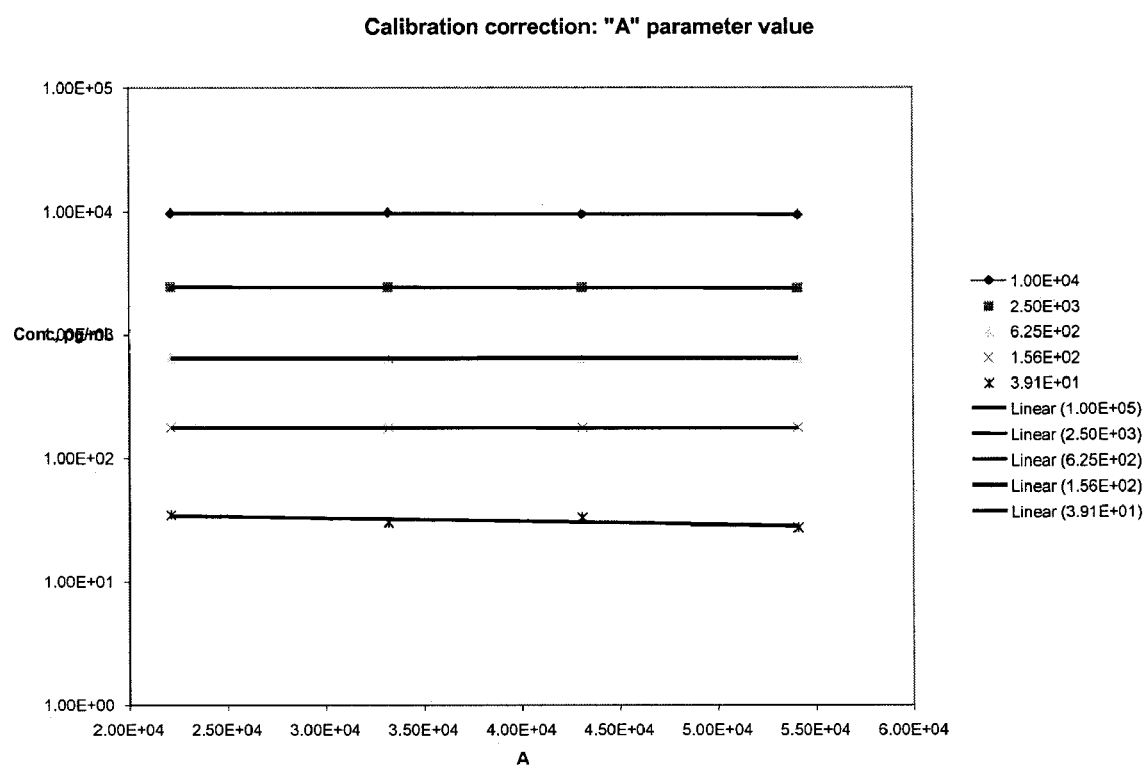
FIG. 18 shows the impact of change in calibration parameter "A" on assay calibration.

The above experimental data were then analyzed by normalizing the assay signal (B) to signal at zero analyte concentration (B0). Using this normalized signal (B/B0), (log-logit) best fits were obtained for each time point and averaged. Concentrations of analyte were computed using these calibration parameters for each time. FIG. 18 shows the derived concentrations that were plotted against the A parameter derived for each individual time point. Each line corresponds to different analyte levels (pg/ml) ranging from about 39 to about 10,000 pg/ml. As can be seen from FIG. 18, although signal values changed by about 2-fold during the course of the experiment, the derived analyte concentration was essentially constant over the analyte concentration spanning a range of about 39 to about 10,000 pg/ml. The variation of calculated concentration was computed and found to average only 2.7% over the calibration range of 39-625 pg/ml (which spans most of the range).

A calibration spike can be enabled by adding analyte to the antibody (or other solid phase capture agent) during manufacturing, and then drying. subsequently adding analyte to the appropriate well during manufacturing (then drying), or adding analyte to a portion of assay buffer which is then routed to the appropriate well. Methods 1 and 2 have a risk which is that the spiked analyte could be flushed from the well as sample or buffer enters. This may be handled in one of several ways such as relying on the tightness of the antigen: antibody interaction for the brief time the well is subject to flowing sample or buffer (which exit from the well), or careful management of liquid flow and placing the spike well as that most distal to the incoming liquid (last well to fill has the least flow through).

Errors in measuring analyte concentrations could also be due to variability in the pre-analysis phase. The primary cause of this type of errors is due to the patient collecting an incorrect volume of sample or where the sample integrity has been compromised. Errors due to incorrect sampling volume can by corrected by a variety of means. One method is to measure the volume of the sample during a pre-processing step. If the measured volume is significantly different from the expected volume, the patient could be instructed to provide a new sample. This could be accomplished by, for example, the wireless communication with the external device as described herein. Alternatively, the analytical methods or algorithms on the external device could be recalibrated to compensate for the change in the sample volume. The recalibration could be using any of the standard calibration techniques or the modifications to the calibration process, which have been described herein.

The following is a description of one embodiment of a method for determining the accuracy of the volume of the sample provided to the sample collection unit of a fluidic device described herein. The sample collection unit can be lined with conductive elements spaced apart at known separations—similar to the graduations on a measuring cylinder or jar. The location of each conductor can correspond to a specific sample volume. As fluid comes into contact with the conductor, the measured conductivity of that conductor would be markedly increased. By identifying the highest placed conductor that has undergone the conductivity change, the volume of the sample in the sample collection unit can be computed.

Alternatively, if the sample volume has to meet a minimum, a conductive element could be placed at the appropriate level in the well. When the cassette is introduced into the handheld (or the sample holder is introduced in the analytical system), thereby the patient has indicated that she has completed the sampling process, and if the conductivity of the sensor remains at the baseline level, it could be easily concluded that the patient has not provided the required sample volume. The patient could be given the appropriate feedback such as replacing the sample or replenishing it. Alternatively, the back-end server or computer at the network headquarters could be informed of the issue and appropriate corrective measures taken. An alternative to the electrical sensing for the correct volume could be using known optical sensing means.

Sample integrity could be affected by many factors, some intrinsic to the patient and some that are extrinsic. Following are some of the sources of errors in sample integrity: (i) mixing of interstitial fluid with blood; (ii) variability in the hematocrit concentration; (iii) hemolysis; and (iv) activation of platelets and sample clotting.

Occasionally, interstitial fluid may leak from a finger-puncture wound and could mix with blood. Alternatively, if the patient had liquid on her hands due to washing prior to obtaining a blood sample, such liquid could also mix with blood plasma. Both fluids mentioned, above, interstitial fluid and wash liquid, contain no red cells and would mix with the blood plasma. When the amount of interstitial fluid is large so that the effective hematocrit is very low, the measured concentration of the external standard (fluorescein) would be low. This signal could be used to conclude that the sample is inappropriate for analysis and that it could lead to incorrect results. When blood is contaminated by water (which has low conductivity), it would be possible to detect this by measuring the conductivity of the fluid part of the sample (blood plasma has a characteristic high conductivity not subject to variation from day-to-day or individual-to-individual). If the measured conductivity of the sample is lower than the plasma conductivity, it is likely that the sample has been contaminated.

Errors could also be due to incorrect operation of the instrument and means of detecting and compensating those errors are described below. One source of error could be that the disposable is not properly accommodated in the handheld system. Having a sensor detect and report the proper mating of the disposable in the handheld would be one means of avoiding this problem. Another source of errors is from the fluidic system, where there may be an issue with where the sample is applied in the sample well and the volume of the applied sample. This could again be addressed by the use of appropriate sensors which detect the application of a sample and report on the adequacy of the volume that is applied. Other fluidics related problems could be blocked channels, insufficient reagents, bubbles, etc., all of which again could be detected and reported by the use of appropriate sensors.

In some embodiments any of the errors described herein can be measured using sensors located on either the fluidic device or the reader assembly. In some embodiments an error messages could be displayed on an LCD screen in the reader assembly using the processing power of the microchip on the handheld. Alternatively, a signal from the sensors could be communicated to the external device which can then relay an error message to either the reader assembly or a third device such as a PDA or cell phone. Such action could be a message communicated to the patient in the form of an audio, video or simple text message that the patient could receive. In some embodiments the external server can transmit corrected calibration parameters to the reader assembly to compensate for any of the errors described herein.

In yet another embodiment, after the identifier is detected by an identifier detector as described herein to determine, for example, a protocol, if a signal transmitted by a sensor doesn't match the expected value for the sensor signal, then the external device can transmit a pre-programmed alert based on each cartridge bar code and sensed signal to either, for example, an LCD display on the reader assembly or to a handheld device, to take a designated action. Nonlimiting examples of error alerts, the problems they indicate, and required action to be taken are, for example:

| Error Code | Symbol | Problem | Action |
| --- | --- | --- | --- |
| Er1 | Thermometer | Temperature out of range | Wait until Temp >10 or <35 C. |
| Er2 | Blood drop | Blood sample too small | If detected w/in 15 minutes of first sample add more blood, other wise use new cartridge |
| Er3 | Battery | Power disruption | Do not start test until power resumes |
| Er4 | Bar code symbol | Cartridge expired | Run test on a non expired cartridge |
| Er5 | Line through fluidic device | Cartridge already used | Run test on a new cartridge |
| Er6 | Phone receiver | No Cell Phone coverage | Do not start test until in coverage area |
| Er7 | Line through a box | Reader malfunction | Call Theranos |
| Er8 | Bottle with a "C" in the label | Calibration overdue | Run Calibration standard, then run test |

After the identifier detector detects the identifier to determine a protocol and any sensed signals are detected and either patient notification is complete or calibration parameter are updated, the fluidic device calibration can occur, followed by the appropriate assay.

Despite the corrective actions described here, the generated analyte concentrations values could still be erroneous. For example, the actual analyte concentration could be well outside the expected range, and thus the calibration parameters used may be incorrect. Values which are unlikely, impossible or inconsistent with prior data for a particularly patient could be flagged and subjected to a software review. Values with suspect accuracy can be communicated to the appropriate decision maker, such as the patient's physician.

Figure 20:
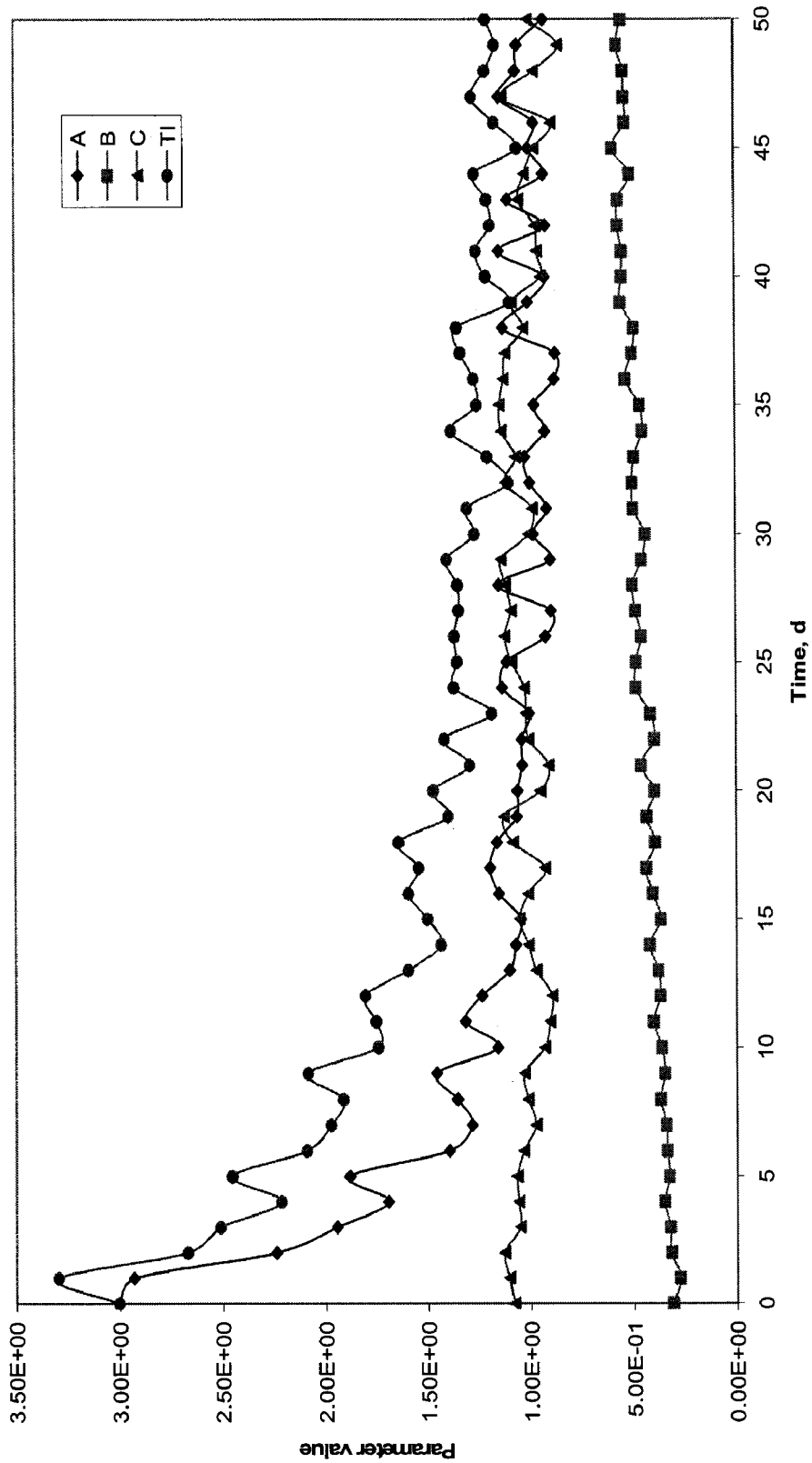
FIG. 20 illustrates computing the therapeutic index.

The concept of the reference therapeutic index (TI) and how it is computed is illustrated in FIGS. 19 and 20. A TI is computed from a retrospective analysis of many measured parameters, including the blood concentrations of drugs of interest, their metabolites, other analytes and biomarkers in blood that change concentrations due to the drugs the patient is consuming, physiologic parameters (such as blood pressure, respiratory rate, body temperature, heart rate, etc.), and clinical parameters that indicate disease progression (such as angina, stroke, infarct, etc.). Typically, many serial measurements would be made for the many treated patient and corresponding controls (unmedicated or placebo treated). The clinical parameter would be an "outcome parameter" (OP). The other measured parameters can be "input parameters" (IP).

For the retrospective analysis and TI computation, data from many subjects and their respective output and input parameters, including subject's relevant details such as height, weight, race, sex, family history, etc., would be populated in a database. Each candidate outcome parameter (stroke, infarct, angina, death, etc.) will be subject to multiple regression analysis against input parameters.

The multiple regression analysis is performed for each candidate OP versus all available IPs. Database columns are constructed by using each IP, each $IP^2$, and all cross-terms ($IP_i*IP_j$). The analysis is then performed using the equation:

$$OP_i = (a*IP1 + b*IP2 + \ldots n*IPn) + (aa*IP1^2 + bb*IP2^2 + \ldots + nn*IPn^2) + (aaa*IP1*IP2 + bbb*IP1*IP3 + \ldots + nnn*IPn-1*IPn),$$

where a ... n, aa ... nn, aaa ... nnn are arbitrary constants.

Multiple regression analysis establishes the best fit to the equation and indicates which IPs are strong candidates for inclusion. Weakly correlated IPs are dropped and the analysis repeated until each candidate OP has an optimal relation to the remaining IPs. The therapeutic index will then have the form:

$$TI = a*IP + cc*IP3^2 + nnn*IP3*IP5 + \quad \text{(Equation 6)}.$$

FIG. 20 illustrates the computation of a TI and the use of the TI concept for determining therapeutic efficacy (the therapeutic index is also indicated by the term efficacy index). The example illustrated in FIG. 20 shows the time course of successful drug therapy of a disease state (such as atherosclerosis) that is indicated by three biochemical analytes represented by parameters A, B and C. The disease is treated (with for example a Statin) starting on day zero.

Parameters A, B and C are measured daily using an ambulatory system as described herein. At the outset, relative to "ideal levels", Parameter A (for example LDL-cholesterol) is elevated, Parameter B (for example HDL-cholesterol) is low and Parameter C (for example, alanine aminotransferase, an indicator of liver damage) is normal. All parameters (A, B, C) are presented normalized to their respective ideal level. As therapy proceeds, the drug causes the levels of A and B to approach normal values but at different rates. Analyte C remains normal indicating the drug is not causing liver damage. The relative risk of an outcome for the patient is represented by an initially unknown TI. As described above, TI is a surrogate to the outcome parameter that reflects the physiological functions of the patient (blood pressure, etc.) or other pre-identified factors in a patient record and can be indicative of improvement in the patient's condition. We further assume that parameter TI is influenced by parameters A and B. In certain cases, at the beginning of the study this relationship remains to be determined.

Data from the monitoring system (device input) and the patient input are analyzed by multiple regression of TI and measured values A, B and C, as described above. In the example shown, these data are analyzed using multiple regression analysis, which fits parameter TI as a function of parameters A, B, C and their squares and the pair-wise cross terms (A*B, etc.) As shown in FIG. 20, for the simulated values shown in FIG. 19, an excellent fit was obtained ($R^2=0.99$) when all parameters were included. It is evident from inspection of the fit that most of the parameters can be eliminated leaving only A and A*B. When this is done the fit is still very good ($R^2=0.95$).

The multiple regression derived function is not identical to the base function which generated the first candidate TI data, but works well to compute an estimate of TI from (typically fewer) measured parameters, prior to clinical validation, if necessary. The appropriate threshold levels of TI, or the optimum TI is termed as $TI_{ref}$ (or "action threshold value".) Expert review can then determine the optimum therapeutic index for that particular patient or patient class. If the computed TI exceeds the preset $TI_{ref}$, appropriate action can be taken. An appropriate action could be alerting the physician, stopping the medication or the like. As can be understood, the appropriate $TI_{ref}$ for a patient would be decided based on the healthcare provider's judgment for that individual patient. The form of the TI is derived as a one time exercise using expert analysis of the data set derived from clinical studies and/or existing clinical information.

Figure 22:
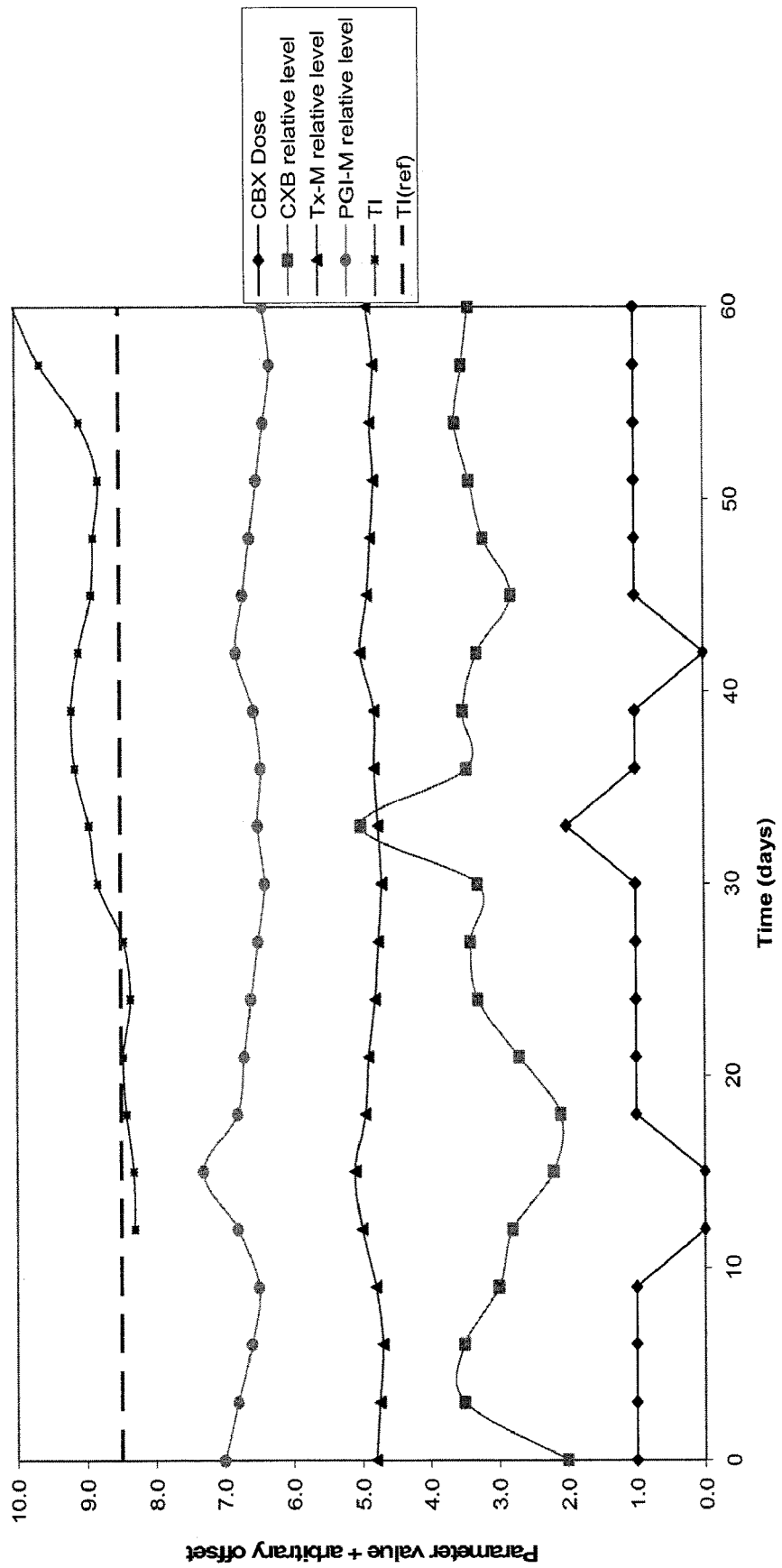
FIG. 22 is an illustration of the relationship between measured drug, analyte and biomarker concentration and therapeutic index.

Once the $TI_{ref}$ is identified, then the use of this parameter is illustrated in FIG. 22. Methods of measuring drug, analyte and biomarker concentrations and conducting a two-way communication with a database using a fluidic device and reader assembly are described in detail herein. The time course of various measured and computed parameters are shown in FIG. 22. The curve indicated CBX Dose illustrates the time course of a drug that is taken on a regular basis. The plotted values are normalized to what would be considered as "ideal levels" for that measurement. For example, if the expected ideal blood concentration of CBX is 100 ng/ml and if the measured concentration in blood is 100 ng/ml, the parameter value is 1.0 (with no offset) for CBX. Similarly, the concentrations of CXB, a metabolite of CBX, biomarkers Tx-M and PGI-M, which vary in response to the concentrations of the drug and the disease state, are also normalized to their ideal values and plotted. All the drug, analyte and biomarker concentrations could be measured using a system as described herein. As explained above, the $TI_{ref}$ for this particular patient is plotted on FIG. 22 as a flat line. Using the parameter values (a ... n, aa ... nn, aaa ... nnn) of Equation 6 and the measured input parameters (IP), the current TI for the patient is calculated. If the computed TI exceeds the $TI_{ref}$ value, then an alert can be generated. The alert could be targeted to the patient's healthcare provider, who in turn can take the appropriate action. An appropriate action could be to watch the patient closely for other clinical indications and/or alter the dosage and drugs the patient is taking.

Figure 23:
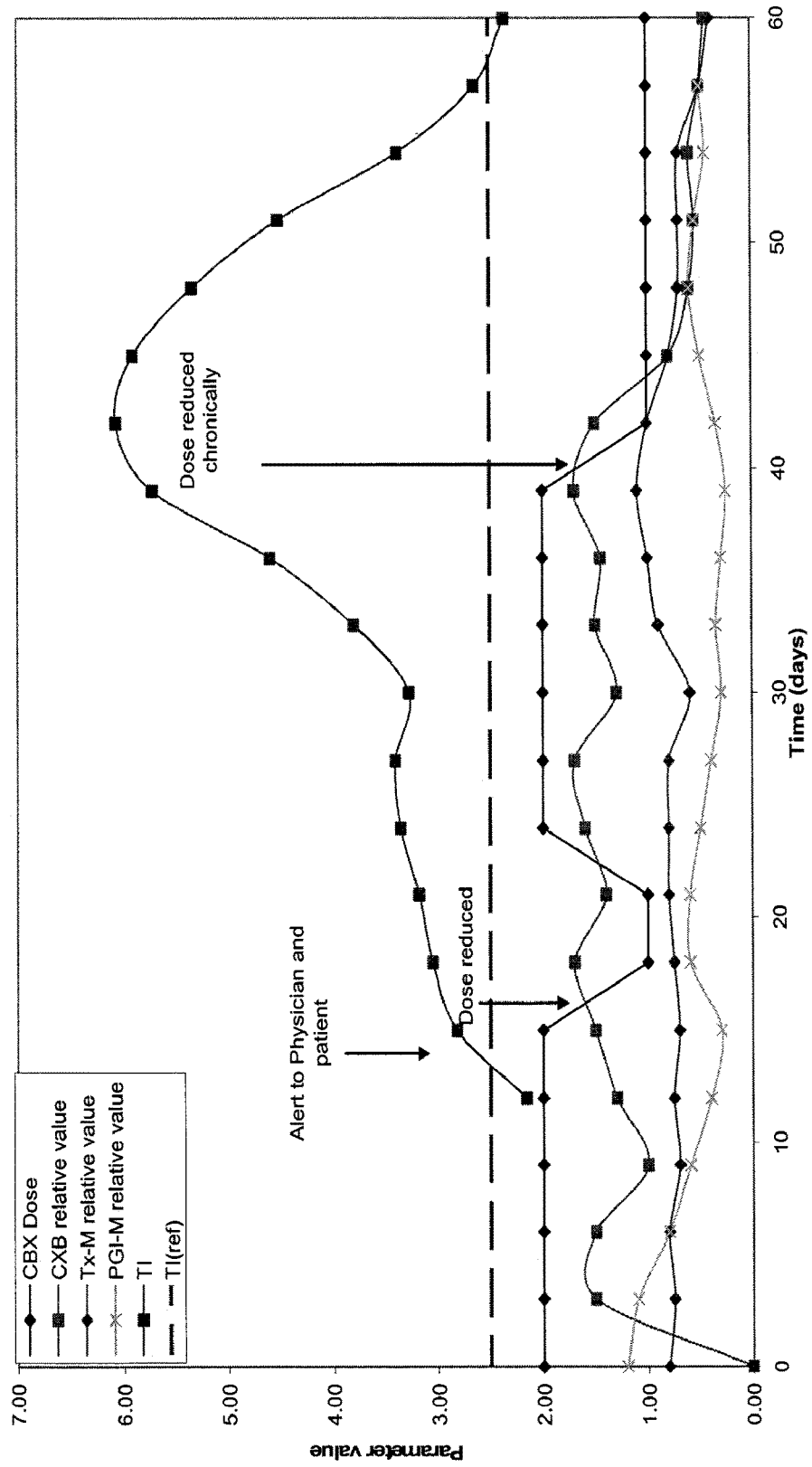
FIG. 23 is an illustration of the application of this invention to minimize adverse drug reactions.

FIGS. 22 and 23 illustrate the concept as to how when the computed TI exceeds the $TI_{ref}$ a proactive action could avert an ADR. In FIG. 23, the patient's TI exceeded $TI_{ref}$ about day 15. The patient is monitored closely and as the TI values continue to increase after day 30, the physician intervenes and reduces the dosage. This action starts lowering the TI for the patient and ultimately retreats to an acceptable level about day 60.

One or more individuals or entities that are involved in the care of the patient (nurses, physicians, pharmacist, etc.) can be alerted when the computed TI exceeds the $TI_{ref}$ so that they could take the appropriate action. Additionally, trends can be discerned and appropriate action taken before a TI reaches a particular value.

In some embodiments many different analytes can be measured and construed as input parameters, IPs, while computing the TI. Such analytes that may be used are described herein. Additionally, the can be expanded or modified depending on the disease area as well. The appropriate list of parameters relating to certain diseases and drug treatments, for example, cancer and infectious diseases and patient on NSAIDS, are disclosed herein.

In another aspect of this invention, the TI is calculated using information derived from the patient's biological sample and patient information that is non-drug related, the device input. For example, in an ambulatory setting, information relating to concentration of drug, metabolite and other biological markers can be detected in blood as described herein. The patient can also input many non-drug related personal parameters. This "patient input" can relate to the patient's personal information, for example, height, weight, gender, daily exercise status, food intake, etc. The patient input could also be provided by the patient's healthcare provider. An example of a patient input parameter and the input means is shown in FIG. 24.

In some embodiments the device input and patient input are used to compute the TI. A reference TI for the patient is already known using retrospective analysis of the data contained in the database. In formulating the TI using multiple regression analysis, the parameters such as those shown in Equation 6 are used. The same parameters are then used with the device input and patient input to compute the TI. Comparing the TI to the $TI_{ref}$, it is possible to determine the efficacy of the therapy. If the TI falls within a predetermined range of $TI_{ref}$, then the treatment is considered to be efficacious. Values below that range indicate that the treatment is ineffective and values higher then the range are considered to be undesirable and could lead to adverse events.

Another example illustrates the implementation of this invention for studying the efficacy of therapy in diseases where it is difficult to make frequent measurements and the efficacy of the treatment is difficult to quantify. An example is determining the efficacy of drug therapy in children with autism. Frequent sampling and concomitant laboratory analysis is impractical for children. Abnormalities in blood concentrations of certain metals are implicated in autism. Hence, following the blood concentration of certain metals, for example, zinc, in autistic children might shed light on the efficacy of an intervention. However, it has been reported that lowered concentrations of Zn, for example, due to a treatment does not imply that the therapy is working. It is an indicator, but not a definitive surrogate for determining therapeutic efficacy. Computing a TI and comparing it to a reference level would better indicate the efficacy. This is illustrated in FIG. 25 by simulating the concentration of various pertinent markers and their change due to a drug intervention in an autistic child.

The program can involve monitoring subjects and matched control individuals over time for toxic metals, surrogate markers for metals (metallothionein, etc.), and other biochemical markers. Subjects are those prone to, or afflicted with autism; controls are situation-matched people. It is not mandatory that there be a situation-matched control. The scenario assumes that during the study a significant "event" occurs. Events could be movement into a more or less risky environment or initiation of therapy. Subjects could be frequently monitored for several parameters (device input) using the ambulatory system described herein. Additional laboratory assays that are not determinable in the ambulatory system could be performed at a lower frequency using laboratory assays. Additional data such as patient information, local environment, use of drugs, diet, etc. would be logged (patient input). Of particular interest to this scenario is information such as exposure to lead, mercury etc.

Figure 25:
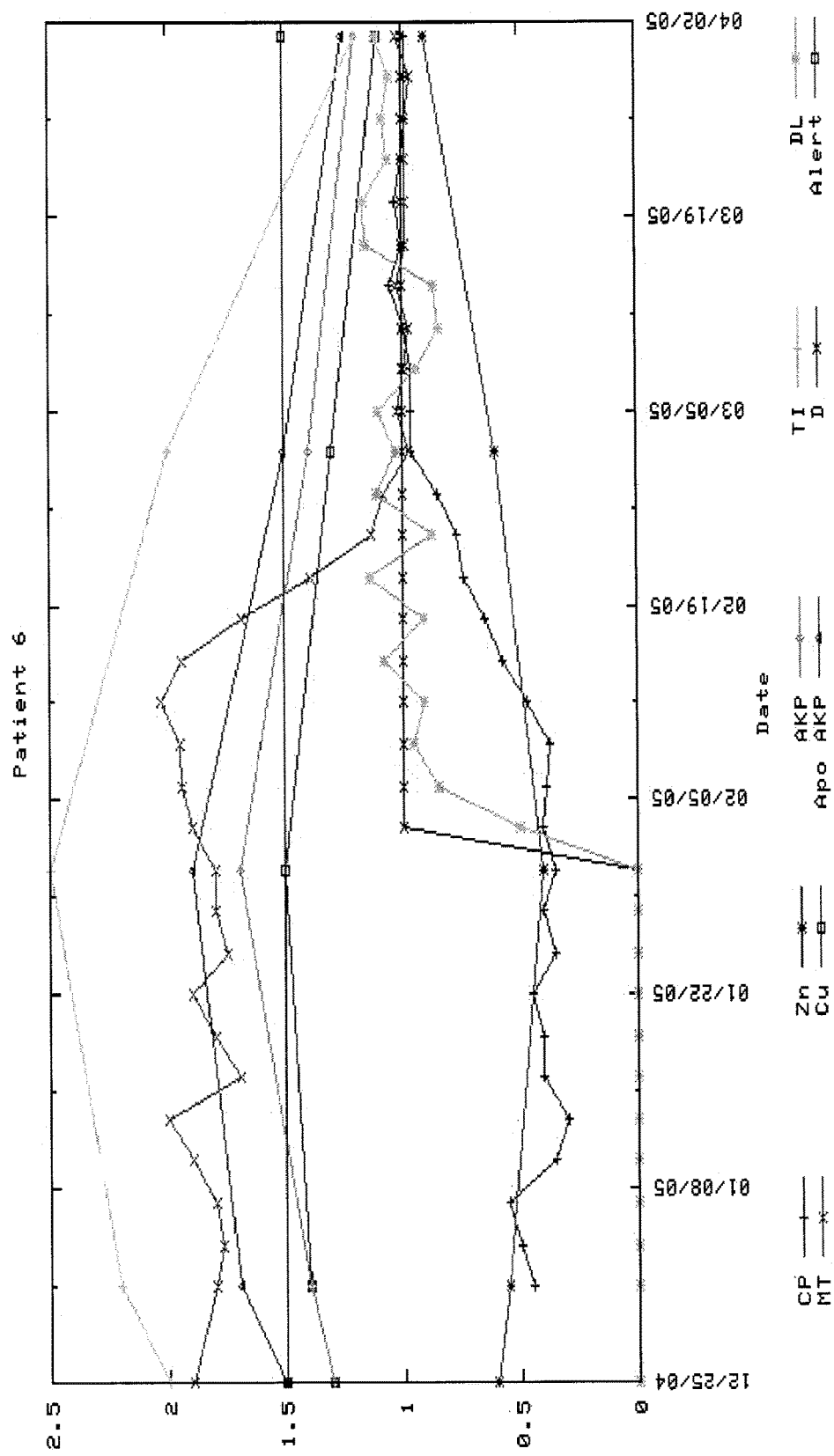
FIG. 25 shows use of a therapeutic index to follow treatment progression in an autism patient.

The time course shown in FIG. 25 envisages an event (initiation of therapy) at 33 days. The subject who is exhibiting abnormal levels of CP and MT, gradually reverts to normal levels of markers. The TI captures the risk or safety level of the subject based on all information. The study will define the best inputs to determine TI.

As described above, TI can be used for determining the efficacy of drug treatment. A similar approach is also well suited for determining the efficacy of drugs during clinical trials. Additionally, this approach could be beneficially used to identify sub-groups of patients who respond well or poorly to a given treatment regimen. The ability to segregate responders from non-responders is an extremely valuable tool. The concept of using TI can be used not only during a therapeutic regimen, but for performing diagnostic tests to determine, for example, whether or not a patient is in need of a biopsy after a complete examination of prostate specific markers.

The invention claimed is:

1. A method comprising:
  inserting a cartridge into a reader assembly, the reader assembly comprising a processor, an analyte signal detector, and a communication interface, the cartridge being configured to be coupled to the reader assembly, the cartridge comprising:
  i) a structure configured to receive a sample;
  ii) a reactant capable of reacting with a biological analyte in the sample; and
  iii) an information storage unit storing identifier information identifying the cartridge;
  obtaining the identifier information from the information storage unit;
  transmitting the identifier information to a computer server, prior to performing an assay using the cartridge coupled to the reader assembly;
  in response to receiving the identifier information, the computer server using the received identifier information to select a protocol from a plurality of protocols stored in the computer server, the selected protocol then being transmitted electronically by the computer server to the communication interface of the reader assembly, wherein the selected protocol comprises instructions to the processor to perform the assay using the cartridge;
  measuring with the analyte signal detector, in accordance with the selected protocol, a first signal produced by a first assay of the sample, wherein the sample comprises a known quantity of the biological analyte;
  measuring a second signal produced by a second assay of the sample after spiking the sample with a known quantity of the biological analyte;
  plotting the difference between said first and second signals against an expected signal representing a target value, wherein the target value is a value expected for the known quantity of the biological analyte;
  computing a best fit of calibration parameters by minimizing the sum of the square of the differences between the target value and calculated analyte values from the first and second signals; and updating a factory calibration parameter of the reader assembly.

2. The method of claim 1, wherein the communication interface is configured to receive the selected protocol wirelessly from the computer server.

3. The method of claim 1, wherein the communication interface is configured to receive the protocol via a wired connection from the computer server.

4. The method of claim 1, further comprising measuring a third signal from the cartridge representative of a presence or non-presence of the biological analyte present in a second sample based a selected protocol received from the computer server.

5. The method of claim 4, wherein the analyte signal detector is configured to detect a luminescent signal.

6. The method of claim 4, wherein the analyte signal detector is configured to detect a chemiluminescent signal.

7. The method of claim 4, the cartridge further comprising a first layer and a second layer, wherein the first and second layers are assembled to form a three dimensional fluidic channel network.

8. The method of claim 4, further comprising:
detecting, via the analyte signal detector, the third signal from the cartridge representative of a presence or non-presence of a biological analyte present in a reaction site based a selected protocol received from the computer server; and
correcting a second calibration parameter in response to the third signal.

9. The method of claim 8, further comprising:
compensating temperature control parameters in response to the correcting of the further calibration parameter prior to detecting via the analyte signal detector, the second signal from the cartridge representative of a presence or non-presence of a biological analyte present in in the second sample based on a selected protocol received from the computer server.

* * * * *